US010548980B2

(12) United States Patent
Levy et al.

(10) Patent No.: US 10,548,980 B2
(45) Date of Patent: Feb. 4, 2020

(54) P2X7 RECEPTOR ANTAGONISTS FOR RESTORING T-CELL LYMPHOPOIESIS IN SUBJECTS INFECTED WITH HUMAN IMMUNODEFICIENCY VIRUS (HIV)

(71) Applicants: INSERM (INSTITUT NATIONAL DE LA SANTÉ ET DE LA RECHERCHE MÉDICALE), Paris (FR); UNIVERSITÉ PARIS-EST CRÉTEIL VAL DE MARNE, Creteil (FR); ASSISTANCE PUBLIQUE-HÔPITAUX DE PARIS (APHP), Paris (FR)

(72) Inventors: Yves Levy, Creteil (FR); Jean-Daniel Lelievre, Creteil (FR); Inna Menkova-Garnier, Creteil (FR)

(73) Assignees: INSERM (Institut National de la Santé et de la Recherche Médicale, Paris (FR); Université Paris-Est Créteil Val de Marne, Créteil (FR); Assistance Publique-Hôpitaux de Paris (APHP), Paris (FR)

( * ) Notice: Subject to any disclaimer, the term of this patent is extended or adjusted under 35 U.S.C. 154(b) by 0 days.

(21) Appl. No.: 16/068,845

(22) PCT Filed: Jan. 13, 2017

(86) PCT No.: PCT/EP2017/050643
§ 371 (c)(1),
(2) Date: Jul. 9, 2018

(87) PCT Pub. No.: WO2017/121840
PCT Pub. Date: Jul. 20, 2017

(65) Prior Publication Data
US 2019/0022223 A1     Jan. 24, 2019

(30) Foreign Application Priority Data
Jan. 14, 2016 (EP) .................................... 16305030

(51) Int. Cl.
A61K 39/00 (2006.01)
A61K 39/395 (2006.01)
C07K 16/28 (2006.01)
C07K 16/24 (2006.01)
C07K 16/18 (2006.01)
A61K 45/00 (2006.01)

(52) U.S. Cl.
CPC .................... A61K 45/00 (2013.01)

(58) Field of Classification Search
CPC .......... A61K 2039/505; A61K 2300/00; C07K 2317/565; C07K 2317/76; C07K 16/241
See application file for complete search history.

(56) References Cited

U.S. PATENT DOCUMENTS

2015/0343011 A1   12/2015   Greene et al.

FOREIGN PATENT DOCUMENTS

| WO | 2002/094317 A1 | 11/2002 |
| WO | 2008/006085 A2 | 1/2008 |
| WO | 2012/019991 A1 | 2/2012 |
| WO | 2013/134030 A1 | 9/2013 |
| WO | WO2013134030 | * 9/2013 |

OTHER PUBLICATIONS

Hazleton et al., "Purinergic receptors are required for HIV-1 infection of primary human macrophages", The journal of immunology, 2012, 188(9):4488-4495.*
J. E. Hazleton et al: "Purinergic Receptors are Required for HIV-1 Infection of Primary Human Macrophages", The Journal of Immunology, vol. 188, No. 9, Mar. 26, 2012, pp. 4488-4495.
Talia H. Swartz et al: "Purinergic Receptors: Key Mediators of Hiv-1 infection and inflammation", Frontiers in Immunology, vol. 7, Nov. 26, 2015, pp. 1-9.
Francesca Graziano et al: "Extracellular ATP induces the rapid release of HIV-1 from virus containing compartments of human macrophages", Proceedings of the National Academy of Sciences, vol. 112, No. 25, Jun. 8, 2015, pp. E3265-E3273.
R. A. North et al: "P2X Receptors as Drug Targets", Molecular Pharmacology, vol. 83, No. 4, Dec. 19, 2012, pp. 759-769.
R. A. North: "Molecular Physiology of P2X Receptors" Physiological Reviews., vol. 82, No. 4, Oct. 1, 2002, pp. 1013-1067.
Inna Menkova-Garnier et al: "P2X7 Receptor Inhibition Improves CD34 T-Cell Differentiation in HIV-Infected Immunological Nonresponders on c-Art", PLOS Pathogens, vol. 12, No. 4, Apr. 15, 2016, p. e1005571.

* cited by examiner

Primary Examiner — Barry A Chestnut
(74) Attorney, Agent, or Firm — W & C IP

(57) ABSTRACT

The present invention relates to pharmaceutical composition and uses thereof for restoring T-cell lymphopoiesis in subjects infected with human immunodeficiency virus (HIV). In particular, the present invention relates to a P2X7 receptor antagonist for use in a method of restoring T-cell lymphopoiesis in a subject infected with human immunodeficiency virus (HIV) comprising administering to the subject a therapeutically effective amount of said P2X7 receptor antagonist.

4 Claims, 9 Drawing Sheets

Figure 3:
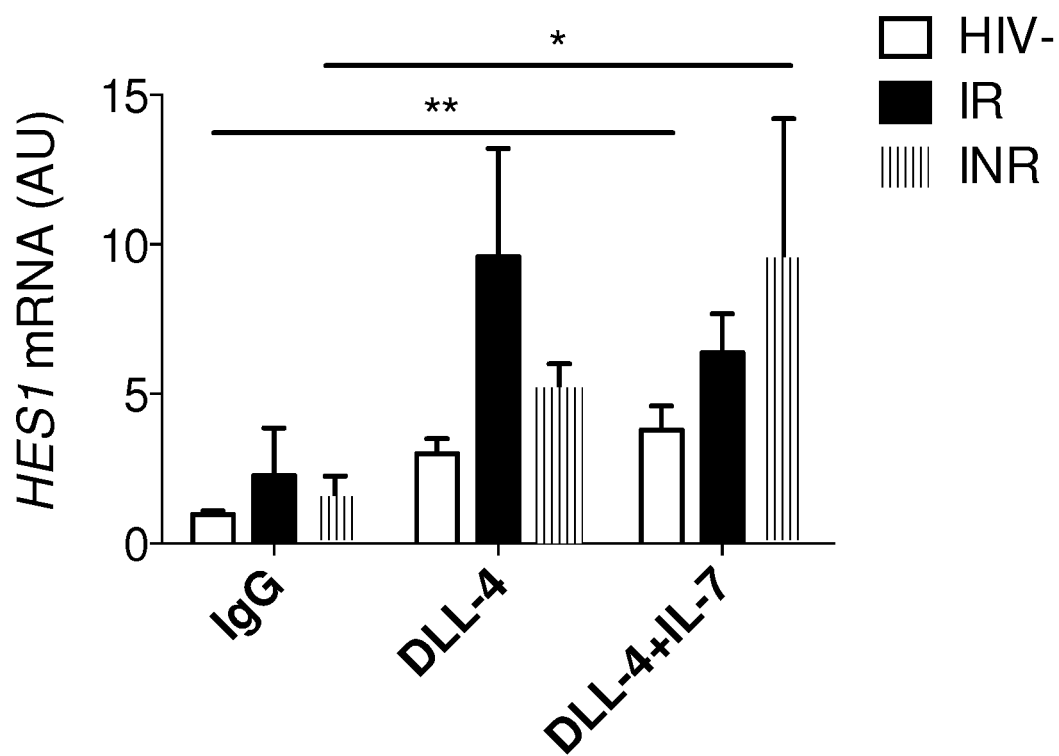

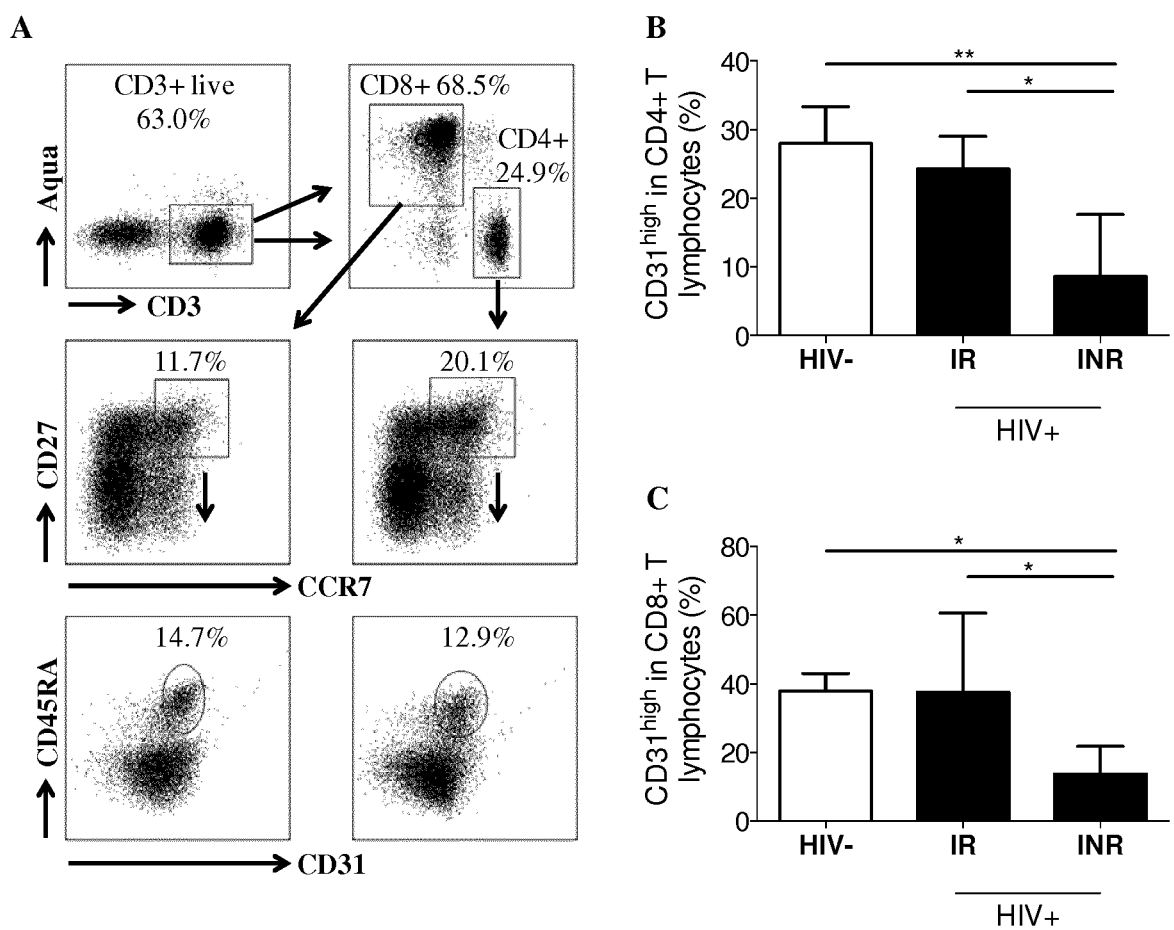
Figures 1A-C

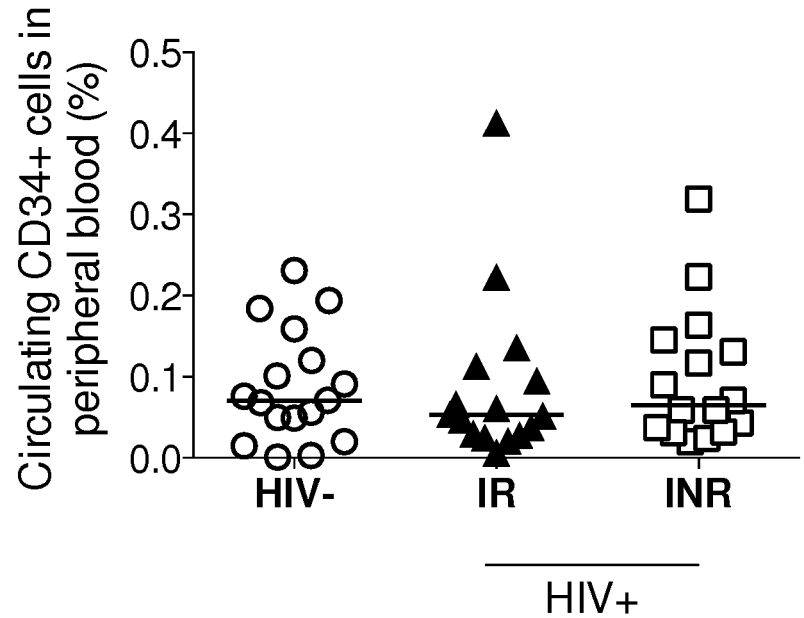
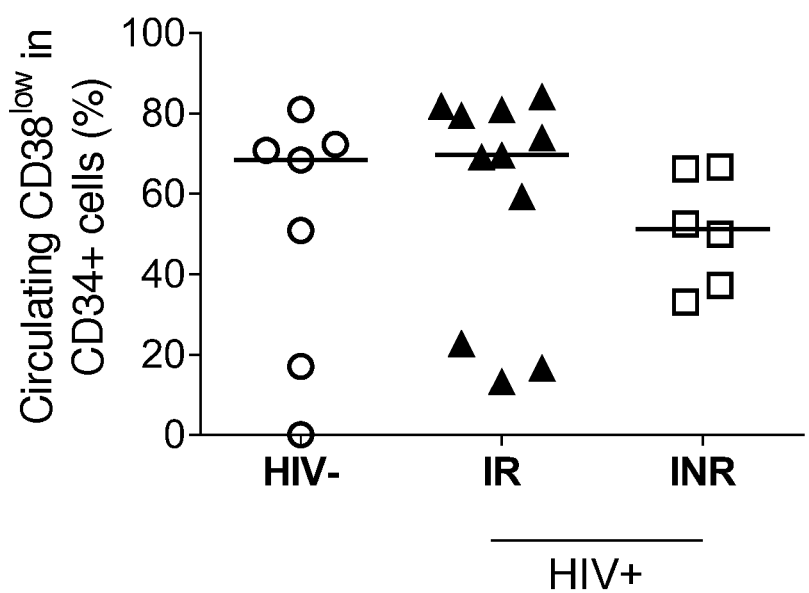
Figures 1D-E

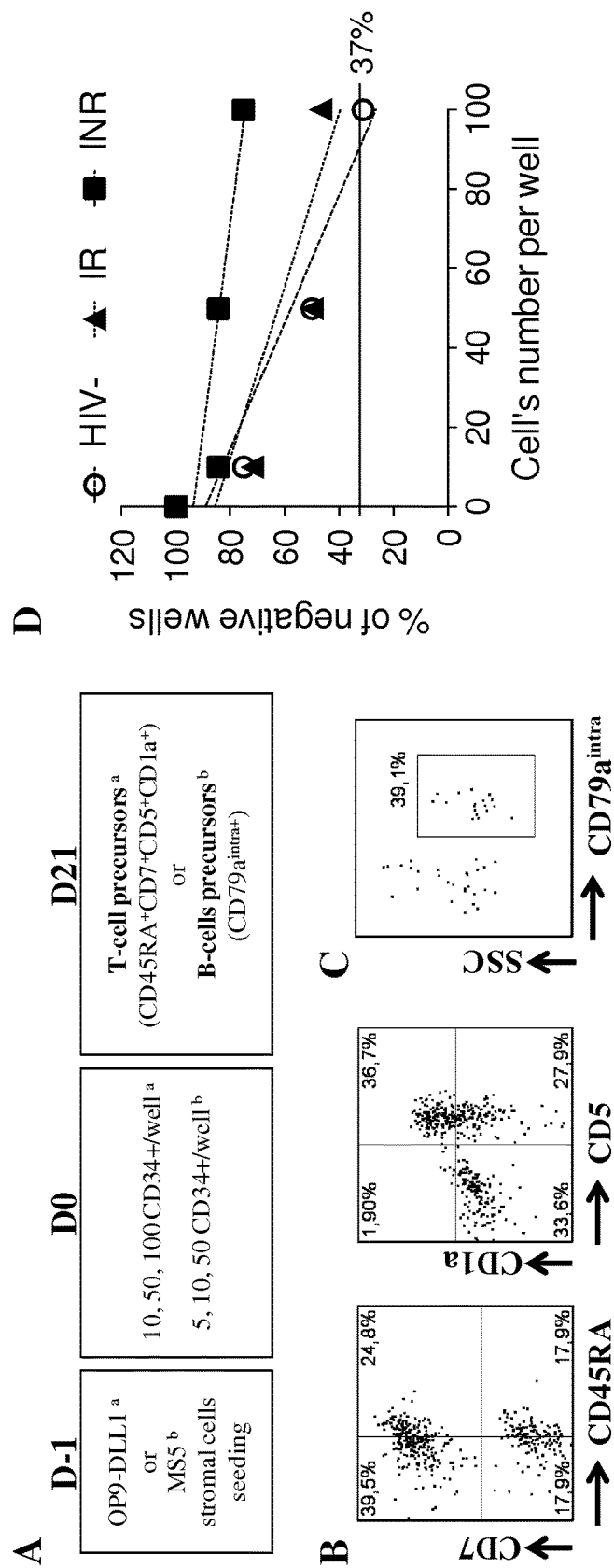
Figures 2A-D

E

| | Cell frequency (1/) | | | P | | |
|---|---|---|---|---|---|---|
| | HIV- | HIV+ IR | HIV+ INR | HIV- vs IR | IR vs INR | HIV- vs INR |
| T-cell potential | 71.9 (54.8-94.5) | 86.3 (67.3-111) | 240.6 (162.1-806.6) | NS | *** | ** |
| B-cell potential | 63.1 (42.5-94.1) | 47 (32.5-68.2) | 64 (42.04-100.1) | NS | NS | NS |

Figure 2E

P2X7 RECEPTOR ANTAGONISTS FOR RESTORING T-CELL LYMPHOPOIESIS IN SUBJECTS INFECTED WITH HUMAN IMMUNODEFICIENCY VIRUS (HIV)

FIELD OF THE INVENTION

The present invention relates to methods and pharmaceutical composition for restoring T-cell lymphopoiesis in subjects infected with human immunodeficiency virus (HIV).

BACKGROUND OF THE INVENTION

Combined antiretroviral treatment (c-ART) has greatly improved the outcome of HIV infection. The key objective of c-ART is to suppress viral replication and to induce the production of sufficient numbers of CD4+ T-cells to prevent AIDS-defining (CD4+ T-cell counts below 200 cells/mm3), and/or non-AIDS-defining (CD4+ T-cell counts below 500 cells/mm3) severe events from occurring (1). Immunological failure is defined as an inability to reach these levels of CD4+ T cells on c-ART. In large cohort of patients displaying viral suppression, immunological success seemed to be largely time-dependent, as the number of CD4+ T-cells seemed to increase steadily, even after seven years (2). CD4+ T-cell restoration may be impeded by mechanisms related to HIV infection and its consequences, or modulated by host factors, both of which may affect T-cell homeostasis either in the periphery or at the level of T-cell production. Demographic factors (age, sex, ethnic group (3-5)) affect CD4+ T-cell levels and, thus, immune restoration. The characteristics of HIV infection in the patient (CD4+ T-cell nadir, peak viral load, duration of infection and viral control on c-ART (4, 6-8)) are also key determinants of CD4+ T-cell recovery. Increases in immune activation (9, 10) and inflammation (11, 12) are currently considered to be the principal mechanisms underlying poor immunological responses on c-ART. Such alterations affect the homeostasis of the T-cell pool, modifying both peripheral and thymic T-cell levels (13). Specific host genetic factors, including polymorphisms of genes of the inflammation/apoptosis pathway (14) or genes involved in T-cell development, such as IL7R (15), have also been associated with poor CD4+ T-cell recovery.

Several studies have shown that HIV may affect CD34+ cells before their colonization of the thymus to generate T lymphocytes (16-18). It remains unclear whether these cells are directly infected (18-24), but it is widely thought that the virus affects the microenvironment of the precursors and stromal cells supporting the architecture of the site (16, 17, 25, 26). Many studies have linked the persistent disturbance of the CD34+ cells by HIV to a decrease in their intrinsic clonogenic potential in humans (17, 20, 25, 27-35) and simian models of infection (26, 36-38). Some of these studies analyzed T-cell development during HIV infection (30, 31, 37-39), but only a few addressed this issue in the context of incomplete immune restoration (17, 34), and none of these studies considered a specific impairment of T-cell development.

SUMMARY OF THE INVENTION

The present invention relates to methods and pharmaceutical composition for restoring T-cell lymphopoiesis in subjects infected with human immunodeficiency virus (HIV). In particular, the present invention is defined by the claims.

DETAILED DESCRIPTION OF THE INVENTION

Even with long-term viral suppression by c-ART, peripheral CD4+ T-cell levels are not fully restored in a significant proportion of HIV+ individuals. These immunological non-responders (INRs) have a higher risk of developing AIDS and non-AIDS events and a lower life expectancy than the general population. The mechanisms underlying this poor recovery are not fully understood. The inventors used an in vitro system to analyze the T- and B-cell potential of CD34+ hematopoietic progenitor cells. Comparisons with control matched HIV+ patients with high CD4+ T-cell counts (immune responders (IRs)) showed that the generation of T-cell progenitors, but not of B-cell progenitors, was impaired in INRs. This impairment resulted in the presence of diminished numbers of recent thymic emigrants (RTE) in the blood and lower peripheral CD4+ T-cell counts. The inventors investigated the molecular pathways involved in lymphopoiesis, focusing particularly on T-cell fate specification (Notch pathway), survival (IL7R-IL7 axis) and death (Fas, P2X7, CD39/CD73). They observed abnormally high levels of P2X7 expression and an absence of CD73 mRNA in the CD34+ cells of INRs, highlighting a role for the ATP pathway. This was confirmed by the demonstration that in vitro inhibition of the P2X7-mediated pathway restored the T-cell potential of CD34+ cells from INRs. Moreover, a transcriptomic analysis of these cells revealed major differences in the cellular survival and death pathways between these cells and CD34+ cells from IRs. These findings raise attractive possibilities for using complementary immunotherapies, such as P2X7 antagonists, to restore T-cell lymphopoiesis in INRs.

Accordingly, a first object of the present invention relates to a method of restoring T-cell lymphopoiesis in a subject infected with human immunodeficiency virus (HIV) comprising administering to the subject a therapeutically effective amount of a P2X7 receptor antagonist.

As used herein, the term "human immunodeficiency virus" or "HIV" can refer to any strain of HIV, including both HIV-1 and HIV-2. The method of the present invention is particular suitable for use in any patient with an HIV infection. In particular, the method of the present invention is suitable for use in any HIV-infected patient in which there is a reasonable likelihood that a therapeutic benefit can be obtained by the use of such method. Such a patient can be characterized as having a sufficient number of "rescueable CD4+ T cells" such that increasing immune responsiveness in these T lymphocytes by the method of the present invention would be reasonably expected to provide a measurable benefit to the patient, alone or in combination with other HIV therapies. In some embodiments, the subject is an immunological non-responders (INR).

As used herein, the term "lymphopoiesis" has its general meaning in the art and refers to the generation of lymphocytes. Thus the term "T-cell lymphopoiesis" refers to the generation of T cells (i.e. lymphocytes T).

A further object of the present invention is a method for the prophylactic treatment of acquired immune deficiency syndrome in a subject infected with human immunodeficiency virus (HIV) comprising administering to the subject a therapeutically effective amount of a P2X7 receptor antagonist.

As used herein, the term "prophylactic treatment" refers to any medical or public health procedure whose purpose is to prevent a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease. It is also to be appreciated that the various modes of treatment or prevention of medical conditions as described are intended to mean "substantial," which includes total but also less than total treatment or prevention, and wherein some biologically or medically relevant result is achieved.

As used herein, the term "P2X7 receptor" has its general meaning in the art and refers to the human receptor described by Rassendren et al. (1997), J. Biol. Chem. 272:5482-5486, as well as any human allelic variants and any mammalian homologs having P2X7 receptor activity and their allelic variants (see also GenBank Accession No. Y09561 and GenBank Accession Nos. Y12851-Y12855). Thus the term "P2X7 receptor antagonist" refers to any compound that is able to inhibit the P2X7 expression or activity. Antagonists of the P2X7 receptor can be identified by several methods known by those skilled in the art. For example, the inhibitory activity of the antagonists of the P2X7 receptor can be determined by their capacity to inhibit the agonist-induced pore formation using the fluorescent dye YO-PRO and Fluorescence Imaging Plate Reader (FLIPR) in THP-1 cells. In general, the agonist used in these identification procedures is BzATP. Similarly, for antagonist activity measurements, the percent maximal intensity induced by a specific concentration of BzATP, and the percent intensities induced in the present of increasing concentrations of antagonists are plotted against each concentration of compound to calculate IC50 values. The potency of the antagonists is inversely proportional to their IC50 value. Methods for assaying for P2X7 receptor antagonism are known in the art, for example from WO200142194 which describes an assay based on the observation that when the P2X7 receptor is activated using a receptor agonist in the presence of ethidium bromide (a fluorescent DNA probe), an increase in the fluorescence of intracellular DNA-bound ethidium bromide is observed.

P2X7 receptor antagonists are well known in the art:

Abberley L, Bebius A, Beswick P J, Billinton A, Collis K L, Dean D K, Fonfria E, Gleave R J, Medhurst S J, Michel A D, Moses A P, Patel S, Roman S A, Scoccitti T, Smith B, Steadman J G, Walter D S. Identification of 2-oxo-N-(phenylmethyl)-4-imidazolidinecarboxamide antagonists of the P2X(7) receptor. Bioorg Med Chem Lett. 2010 Nov. 15; 20(22):6370-4.

Abdi M H, Beswick P J, Billinton A, Chambers L J, Charlton A, Collins S D, Collis K L, Dean D K, Fonfria E, Gleave R J, Lejeune C L, Livermore D G, Medhurst S J, Michel A D, Moses A P, Page L, Patel S, Roman S A, Senger S, Slingsby B, Steadman J G, Stevens A J, Walter D S. Discovery and structure-activity relationships of a series of pyroglutamic acid amide antagonists of the P2X7 receptor. Bioorg Med Chem Lett. 2010 Sep. 1; 20(17): 5080-4.

Chambers L J, Stevens A J, Moses A P, Michel A D, Walter D S, Davies D J, Livermore D G, Fonfria E, Demont E H, Vimal M, Theobald P J, Beswick P J, Gleave R J, Roman S A, Senger S. Synthesis and structure-activity relationships of a series of (1H-pyrazol-4-yl)acetamide antagonists of the P2X7 receptor. Bioorg Med Chem Lett. 2010 May 15; 20(10):3161-4.

Chen X, Pierce B, Naing W, Grapperhaus M L, Phillion D P. Discovery of 2-chloro-N-((4,4-difluoro-1-hydroxycyclohexyl)methyl)-5-(5-fluoropyrimidin-2-yl)benzamide as a potent and CNS penetrable P2X7 receptor antagonist. Bioorg Med Chem Lett. 2010 May 15; 20(10):3107-11.

Duplantier A J, Dombroski M A, Subramanyam C, Beaulieu A M, Chang S P, Gabel C A, Jordan C, Kalgutkar A S, Kraus K G, Labasi J M, Mussari C, Perregaux D G, Shepard R, Taylor T J, Trevena K A, Whitney-Pickett C, Yoon K. Optimization of the physicochemical and pharmacokinetic attributes in a 6-azauracil series of P2X7 receptor antagonists leading to the discovery of the clinical candidate CE-224,535. Bioorg Med Chem Lett. 2011 Jun. 15; 21(12):3708-11.

Gleave R J, Walter D S, Beswick P J, Fonfria E, Michel A D, Roman S A, Tang S P. Synthesis and biological activity of a series of tetrasubstituted-imidazoles as P2X(7) antagonists. Bioorg Med Chem Lett. 2010 Aug. 15; 20(16):4951-4.

Keystone E C, Wang M M, Layton M, Hollis S, McInnes I B; D1520000001 Study Team. Clinical evaluation of the efficacy of the P2X7 purinergic receptor antagonist AZD9056 on the signs and symptoms of rheumatoid arthritis in patients with active disease despite treatment with methotrexate or sulphasalazine. Ann Rheum Dis. 2012 October; 71(10):1630-5.

Kwak S H, Lee W G, Lee Y J, Lee S D, Kim Y C, Ko H. Discovery of novel purine-based heterocyclic P2X7 receptor antagonists. Bioorg Chem. 2015 August; 61:58-65.

Lee W G, Lee S D, Cho J H, Jung Y, Kim J H, Hien T T, Kang K W, Ko H, Kim Y C Structure-activity relationships and optimization of 3,5-dichloropyridine derivatives as novel P2X(7) receptor antagonists. J Med Chem. 2012 Apr. 26; 55(8):3687-98.

Nelson D W, Sarris K, Kalvin D M, Namovic M T, Grayson G, Donnelly-Roberts D L, Harris R, Honore P, Jarvis M F, Faltynek C R, Carroll W A. Structure-activity relationship studies on N'-aryl carbohydrazide P2X7 antagonists. J Med Chem. 2008 May 22; 51(10):3030-4.

Park J H, Lee G E, Lee S D, Ko H, Kim Y C. Structure-activity relationship studies of pyrimidine-2,4-dione derivatives as potent P2X7 receptor antagonists. Eur J Med Chem. 2015 Dec. 1; 106:180-93.

Romeo Romagnoli, Pier Giovanni Baraldi & Francesco Di Virgilio Recent progress in the discovery of antagonists acting at P2X7 receptor Expert Opinion on Therapeutic Patents Volume 15, Issue 3, March 2005, pages 271-287).

Stock T C, Bloom B J, Wei N, Ishaq S, Park W, Wang X, Gupta P, Mebus C A. Efficacy and safety of CE-224,535, an antagonist of P2X7 receptor, in treatment of patients with rheumatoid arthritis inadequately controlled by methotrexate. J Rheumatol. 2012 April; 39(4):720-7.

Examples of P2X7 receptor antagonists which may be used in accordance with the present invention are described in WO200061569, WO200142194, WO200144170, WO200144213, WO200146200, WO200194338, WO2003041707, WO2003042190, WO2003042191, WO2003047515, WO2003080579, WO2003080579, WO2004058270, WO2004058731, WO2004074224, WO2004099146, WO2004105796, WO2004105797, WO2004105798, WO2004106305, WO2005009968, WO2005014529, WO2005014555, WO2005019182, WO2005111003, WO2006017406, WO2006025783, WO2006059945, WO2006059945, WO2006083214, WO2006086229, WO2006102588, WO2006102610, WO2006110516, WO2007028022, WO2007056046, WO2007056091, WO2007056091, WO2008005368, WO2008124153, WO2009070116, WO2009132000, WO2011054947, WO2012040048, WO2013178783, WO2014097140, WO2014115072, and WO2014115078 the entire contents of which are incorporated herein by reference.

In some embodiments, the P2X7 receptor antagonist is selected from the group consisting of
4-Chloro-1H-indole-5-carboxylic acid ((S)-1-cyclohexyl-2-hydroxy-ethyl)-amide;
4-Chloro-1H-indole-5-carboxylic acid (1-hydroxy-cyclohexylmethyl)-amide;
4-Chloro-1H-indole-5-carboxylic acid (1-hydroxy-cycloheptylmethyl)-amide;
4-Chloro-1H-indole-5-carboxylic acid (4,4-difluoro-1-hydroxy-cyclohexylmethyl)-amide;
4-Chloro-1H-indole-5-carboxylic acid [(S)-1-(4,4-difluoro-cyclohexyl)-2-hydroxy-ethyl]-amide;
4-Chloro-1-methyl-1H-indole-5-carboxylic acid (1-hydroxy-cyclohexylmethyl)-amide;
4-Chloro-1-methyl-1H-indole-5-carboxylic acid ((S)-1-cyclo hexyl-2-hydroxy-ethyl)-amide;
4-Chloro-3-formyl-1H-indole-5-carboxylic acid ((S)-1-cyclo hexyl-2-hydroxy-ethyl)-amide;
4-Chloro-3-formyl-1H-indole-5-carboxylic acid (1-hydroxy-cyclohexylmethyl)-amide;
4-Chloro-1H-indole-5-carboxylic acid (1-cycloheptyl-2-hydroxy-ethyl)-amide;
4-Chloro-1H-indole-5-carboxylic acid [1-(2-trifluoromethyl-pyrimidin-5-yl)-cyclohexylmethyl]-amide;
4-Chloro-1H-indole-5-carboxylic acid [1-(6-chloro-pyridin-3-yl)-cyclohexylmethyl]-amide;
4-Chloro-1H-indole-5-carboxylic acid [1-(6-trifluoromethyl-pyridin-3-yl)-cyclohexylmethyl]-amide;
4-Chloro-1H-indole-5-carboxylic acid [1-(6-chloro-pyridin-3-yl)-4,4-difluoro-cyclohexylmethyl]-amide;
4-Chloro-1H-indole-5-carboxylic acid [1-(4-chloro-phenyl)-cyclohexylmethyl]-amide;
4-Chloro-1H-indole-5-carboxylic acid [1-(4-trifluoromethyl-phenyl)-cyclohexylmethyl]-amide;
4-Chloro-1H-indole-5-carboxylic acid (1-pyridin-3-yl-cyclohexylmethyl)-amide;
4-Chloro-1H-indole-5-carboxylic acid (1-pyridin-3-yl-cyclopentylmethyl)-amide;
4-Chloro-1H-indole-5-carboxylic acid (1-pyridin-3-yl-cycloheptylmethyl)-amide;
4-Chloro-7-methyl-1H-indole-5-carboxylic acid (1-hydroxy-cyclohexylmethyl)-amide;
4-Chloro-2-oxo-2,3-dihydro-1H-indole-5-carboxylic acid (1-hydroxy-cycloheptylmethyl)-amide;
4-Chloro-2-methyl-1H-indole-5-carboxylic acid (1-hydroxy-cyclohexylmethyl)-amide;
4-Chloro-7-iodo-3-methylsulfanyl-1H-indole-5-carboxylic acid (1-hydroxy-cyclohexylmethyl)-amide;
4-Chloro-7-methyl-1H-indole-5-carboxylic acid (4,4-difluoro-1-hydroxy-cyclohexylmethyl)-amide;
4-Chloro-7-methyl-1H-indole-5-carboxylic acid (1-hydroxy-cycloheptylmethyl)-amide;
4-Chloro-3-fluoro-1H-indole-5-carboxylic acid (1-hydroxy-cycloheptylmethyl)-amide; 4-Methoxy-1H-indole-5-carboxylic acid (1-hydroxy-cycloheptylmethyl)-amide;
3,4-Dichloro-1H-indole-5-carboxylic acid (1-hydroxy-cyclohexylmethyl)-amide;
4-Chloro-7-nitro-1H-indole-5-carboxylic acid (1-hydroxy-cyclohexylmethyl)-amide;
1-{[(4-Chloro-1H-indole-5-carbonyl)-amino]-methyl}-cyclohexanecarboxylic acid methyl ester;
4-Chloro-1H-indole-5-carboxylic acid (1-hydroxymethyl-cyclohexylmethyl)-amide;
7-Amino-4-chloro-1H-indole-5-carboxylic acid (1-hydroxy-cyclohexylmethyl)-amide;
4-Chloro-3-methyl-1H-indole-5-carboxylic acid (1-hydroxy-cycloheptylmethyl)-amide;
4-Chloro-1H-indole-5-carboxylic acid (1-carbamoyl-cyclohexylmethyl)-amide;
4-Chloro-1H-indole-5-carboxylic acid (1-methylcarbamoyl-cyclohexylmethyl)-amide;
4-Chloro-1H-indole-5-carboxylic acid (1-cyano-cyclohexylmethyl)-amide;
(1-{[(4-Chloro-1H-indole-5-carbonyl)-amino]-methyl}-cyclohexyl)-carbamic acid tert-butyl ester;
4,6-Dichloro-1H-indole-5-carboxylic acid (4,4-difluoro-1-hydroxy-cyclohexylmethyl)-amide;
4-Chloro-1H-indole-5-carboxylic acid (1-amino-cyclohexylmethyl)-amide;
4-Chloro-6-methyl-1H-indole-5-carboxylic acid (1-hydroxy-cyclohexylmethyl)-amide;
4-Chloro-1H-indole-5-carboxylic acid (1-hydroxy-cyclopentylmethyl)-amide;
4-Chloro-1H-indole-5-carboxylic acid (1-hydroxy-cyclooctylmethyl)-amide;
4-Chloro-1H-indole-5-carboxylic acid (1-methoxy-cyclohexylmethyl)-amide;
4-Chloro-1H-indole-5-carboxylic acid ((S)-1-cyclohexyl-ethyl)-amide;
4-Chloro-1H-indole-5-carboxylic acid ((R)-1-cyclohexyl-ethyl)-amide;
4-Chloro-1H-indole-5-carboxylic acid (1-acetylamino-cyclohexylmethyl)-amide;
4-Chloro-1H-indole-5-carboxylic acid (1-methanesulfonylarnino-cyclohexylrnethyl)-arTiide;
4-Chloro-1H-indole-5-carboxylic acid (1-dimethylamino-cyclohexylmethyl)-amide;
4-Chloro-1H-indole-5-carboxylic acid (1-benzylamino-cyclohexylmethyl)-amide;
3-Bromo-4-chloro-7-methyl-1H-indole-5-carboxylic acid (1-hydroxy-cyclohexylmethyl)-amide;
(1-{[(4-Chloro-1H-indole-5-carbonyl)-amino]-methyl}-cyclohexylsulfamoyl)-acetic acid methyl ester;
4-Chloro-7-isobutyl-1H-indole-5-carboxylic acid (1-hydroxy-cycloheptylmethyl)-amide; 4-Chloro-7-(3-methoxy-propyl)-1H-indole-5-carboxylic acid (1-hydroxy-cycloheptylmethyl)-amide;
4-Chloro-7-isobutyl-1H-indole-5-carboxylic acid (4,4-difluoro-1-hydroxy-cyclohexylmethyl)-amide;
4-Chloro-7-(3-methoxy-propyl)-1H-indole-5-carboxylic acid (4,4-difluoro-1-hydroxy-cyclohexylmethyl)-amide;
4-Chloro-1H-indole-5-carboxylic acid [1-(2-hydroxy-ethanesulfonylamino)-cyclohexylmethyl]-amide; 4-Methyl-1H-indole-5-carboxylic acid (1-hydroxy-cyclohexylmethyl)-amide;
4-Chloro-1H-indole-5-carboxylic acid [1-(2-methyl-pyrimidin-5-yl)-cyclohexylmethyl]-amide;
4-Chloro-7-methoxy-1H-indole-5-carboxylic acid (4,4-difluoro-1-hydroxy-cyclohexylmethyl)-amide;
4-Chloro-1H-indole-5-carboxylic acid [4,4-difluoro-1-(2-methyl-pyrimidin-5-yl)-cyclohexylmethyl]-amide;
4-Chloro-7-methyl-1H-indole-5-carboxylic acid [4,4-difluoro-1-(2-methyl-pyrimidin-5-yl)-cyclohexylmethyl]-amide;
4-Chloro-7-methyl-1H-indole-5-carboxylic acid [1-(2-methyl-pyrimidin-5-yl)-cyclohexylmethyl]-amide;
4,7-Dimethyl-1H-indole-5-carboxylic acid (4,4-difluoro-1-hydroxy-cyclohexylmethyl)-amide; and 4-Methyl-1H-indole-5-carboxylic acid (4,4-difluoro-1-hydroxy-cyclohexylmethyl)-amide; or salts (in particular pharmaceutically acceptable salts) of such compounds;

In some embodiments, the P2X7 receptor antagonist is selected from the group consisting of:

N'-cyano-2-(2-methylphenyl)-N-[(1R)-1-phenylethyl]ethanimidamide,
N'-cyano-2-(2-methylphenyl)-N-(1-methyl-1-phenylethyl)ethanimidamide,
N'-cyano-N-[(1R)-1-(4-fluorophenyl)ethyl]-2-(2-methylphenyl)ethanimidamide,
N'-cyano-2-(2-methylphenyl)-N-[(1R)-1-phenylpropyl]ethanimidamide,
N'-cyano-N-[(1R)-1-(2-fluorophenyl)ethyl]-2-(2-methylphenyl)ethanimidamide,
N'-cyano-N-[1-(3-fluorophenyl)ethyl]-2-(2-methylphenyl)ethanimidamide,
N'-cyano-N-[1-(3,5-difluorophenyl)ethyl]-2-(2-methylphenyl)ethanimidamide,
N'-cyano-N-[3-(4-methoxyphenyl)-1-methylpropyl]-2-(2-methylphenyl)ethanimidamide,
N'-cyano-2-(2-methylphenyl)-N-[(1R)-1-phenylpropyl]ethanimidamide,
N-[2-(2-chlorophenyl)-2-(dimethylamino)ethyl]-N'-cyano-2-(2-methylphenyl)ethanimidamide,
N'-cyano-N-[1-(4-fluorophenyl)ethyl]-2-(2-methylphenyl)ethanimidamide,
N-[2-(2-chlorophenyl)ethyl]-N'-cyano-2-(2-methylphenyl)ethanimidamide,
N'-cyano-2-(2-methylphenyl)-N-(2-morpholin-4-yl-1-phenylethyl)ethanimidamide,
N'-cyano-2-(2-methylphenyl)-N-[1-(2-morpholin-4-ylphenyl)ethyl]ethanimidamide,
N'-cyano-N-(2-methylbenzyl)-3-phenylbutanimidamide, and
N1-cyano-N-[1-(3,5-difluorophenyl)ethyl]-2-[2-(trifluoromethyl)phenyl]ethanimidamide.

In some embodiments, the P2X7 receptor antagonist is selected from the group consisting of:

2-Chloro-5-[[2-(2-hydroxy-ethylamino)-ethylamino]-methyl]-N-(tricyclo [3.3.1.13'7]dec-1-ylmethyl)-benzamide,
2-Chloro-5-[3-[(3-hydroxypropyl)amino]propyl]-N-(tricyclo[3.3.1.1]dec-1-ylmethyl)-benzamide,
(R)-2-Chloro-5-[3-[(2-hydroxy-1-methylethyl)amino]propyl]-N-(tricyclo[3.3.1.13'7]dec-1-ylmethyl)-benzamide,
2-Chloro-5-[[2-[(2-hydroxyethyl)amino]ethoxy]methyl]-N-(tricyclo[3.3.1.13,7]dec-1-ylmethyl)-benzamide,
2-Chloro-5-[3-[3-(methylamino)propoxy]propyl]-N-(tricyclo[3.3.1.13,7]dec-1-ylmethyl)benzamide,
2-Chloro-5-[3-(3-hydroxy-propylamino)-propoxy]-N-(tricyclo[3.3.1.13'7]dec-1-ylmethyl)-benzamide,
2-Chloro-5-[2-(3-hydroxypropylamino)ethylamino]-N-(tricyclo[3.3.1.13'7]dec-1-ylmethyl)-benzamide,
2-Chloro-5-[2-(3-hydroxypropylsulfonyl)ethoxy]-N-(tricyclo[3.3.1.13'7]dec-1-ylmethyl)-benzamide,
2-Chloro-5-[2-[2-[(2-hydroxyethyl)amino]ethoxy]ethoxy]-N-(tricyclo[3.3.1.13,7]dec-1-ylmethyl)-benzamide,
2-Chloro-5-[[2-[[2-(1-methyl-1H-imidazol-4-yl)ethyl]amino]ethyl]amino]-N-(tricyclo[3.3.1.137]dec-1-ylmethyl)-benzamide,
2-Chloro-5-piperazin-1-ylmethyl-N-(tricyclo[3.3.1.1]dec-1-ylmethyl)-benzamide,
3 7 2-Chloro-5-(4-piperidinyloxy)-N-(tricyclo[3.3.1.1']dec-1-ylmethyl)-benzamide,
2-Chloro-5-(2,5-diazabicyclo[2.2.1]hept-2-ylmethyl)-N-(tricyclo[3.3.1.1]dec-1-ylmethyl)-benzamide,
3 7 2-Chloro-5-(piperidin-4-ylsulfinyl)-N-(tricyclo[3.3.1.1']dec-1-ylmethyl)-benzamide,
5-Chloro-2-[3-[(3-hydroxypropyl)amino]propyl]-N-(tricyclo[3.3.1.13,7]dec-1-ylmethyl)-4-pyridinecarboxamide,
2-Chloro-5-[3-[[(1R)-2-hydroxy-1-methylethyl]amino]propyl]-N-(tricyclo[3.3.1.13'7]dec-1-ylmethyl)-3-pyridinecarboxamide,
5-Chloro-2-[3-(ethylamino)propyl]-N-(tricyclo[3.3.1.13,7]dec-1-ylmethyl)-4-pyridinecarboxamide,
5-Chloro-2-[3-[(2-hydroxyethyl)amino]propyl]-N-(tricyclo[3.3.1.13'7]dec-1-ylmethyl)-4-pyridinecarboxamide,
5-Chloro-2-[3-[[(2S)-2-hydroxypropyl]amino]propyl]-N-(tricyclo[3.3.1.13'7]dec-1-ylmethyl)-4-pyridinecarboxamide,
N-[2-Methyl-5-(9-oxa-3,7-diazabicyclo[3.3.1]non-3-ylcarbonyl)phenyl]-tricyclo[3.3.1.13'7]decane-1-acetamide, or a pharmaceutically acceptable salt or solvate of any one thereof.

In some embodiments, the P2X7 receptor antagonist is selected from the group consisting of 2-Chloro-5-[[2-(2-hydroxy-ethylamino)-ethylamino]-methyl]-N-(tricyclo [3.3.1.13'7]dec-1-ylmethyl)-benzamide,
2-Chloro-5-[3-[(3-hydroxypropyl)amino]propyl]-N-(tricyclo[3.3.1.1]dec-1-ylmethyl)-benzamide,
(R)-2-Chloro-5-[3-[(2-hydroxy-1-methylethyl)amino]propyl]-N-(tricyclo[3.3.1.13'7]dec-1-ylmethyl)-benzamide,
2-Chloro-5-[[2-[(2-hydroxyethyl)amino]ethoxy]methyl]-N-(tricyclo[3.3.1.13'7]dec-1-ylmethyl)-benzamide,
2-Chloro-5-[3-[3-(methylamino)propoxy]propyl]-N-(tricyclo[3.3.1.13,7]dec-1-ylmethyl)benzamide,
2-Chloro-5-[3-(3-hydroxy-propylamino)-propoxy]-N-(tricyclo[3.3.1.13'7]dec-1-ylmethyl)-benzamide,
2-Chloro-5-[2-(3-hydroxypropylamino)ethylamino]-N-(tricyclo[3.3.1.13'7]dec-1-ylmethyl)-benzamide,
2-Chloro-5-[2-(3-hydroxypropylsulfonyl)ethoxy]-N-(tricyclo[3.3.1.13'7]dec-1-ylmethyl)-benzamide,
2-Chloro-5-[2-[2-[(2-hydroxyethyl)amino]ethoxy]ethoxy]-N-(tricyclo[3.3.1.13,7]dec-1-ylmethyl)-benzamide,
2-Chloro-5-[[2-[[2-(1-methyl-1H-imidazol-4-yl)ethyl]amino]ethyl]amino]-N-(tricyclo[3.3.1.13,7]dec-1-ylmethyl)-benzamide,
2-Chloro-5-piperazin-1-ylmethyl-N-(tricyclo[3.3.1.1]dec-1-ylmethyl)-benzamide,
3 7 2-Chloro-5-(4-piperidinyloxy)-N-(tricyclo[3.3.1.1']dec-1-ylmethyl)-benzamide,
2-Chloro-5-(2,5-diazabicyclo[2.2.1]hept-2-ylmethyl)-N-(tricyclo[3.3.1.1]dec-1-ylmethyl)-benzamide,
2-Chloro-5-(piperidin-4-ylsulfinyl)-N-(tricyclo[3.3.1.1']dec-1-ylmethyl)-benzamide,
5-Chloro-2-[3-[(3-hydroxypropyl)amino]propyl]-N-(tricyclo[3.3.1.13'7]dec-1-ylmethyl)-4-pyridinecarboxamide,
2-Chloro-5-[3-[[(1R)-2-hydroxy-1-methylethyl]amino]propyl]-N-(tricyclo [3.3.1.13,?]dec-1-ylmethyl)-3-pyridinecarboxamide,
5-Chloro-2-[3-(ethylamino)propyl]-N-(tricyclo[3.3.1.13,7]dec-1-ylmethyl)-4-pyridinecarboxamide,
5-Chloro-2-[3-[(2-hydroxyethyl)amino]propyl]-N-(tricyclo [3.3.1.13'7]dec-1-ylmethyl)-4-pyridinecarboxamide,
5-Chloro-2-[3-[[(2S)-2-hydroxypropyl]amino]propyl]-N-(tricyclo[3.3.1.13'7]dec-1-ylmethyl)-4-pyridinecarboxamide,
N-[2-Methyl-5-(9-oxa-3,7-diazabicyclo[3.3.1]non-3-ylcarbonyl)phenyl]-tricyclo[3.3.1.13'7]decane-1-acetamide, or a pharmaceutically acceptable salt or solvate of any one thereof.

In some embodiments, the P2x7 receptor antagonist is selected from the group consisting of
2-Chloro-5-[[2-(2-hydroxy-ethylamino)-ethylamino]-methyl]-N-(tricyclo [3.3.1.13'7]dec-1-ylmethyl)-benzamide,
2-Chloro-5-[3-[(3-hydroxypropyl)amino]propyl]-N-(tricyclo[3.3.1.1]dec-1-ylmethyl)-benzamide,
(R)-2-Chloro-5-[3-[(2-hydroxy-1-methylethyl)amino]propyl]-N-(tricyclo[3.3.1.13'7]dec-1-ylmethyl)-benzamide,
2-Chloro-5-[[2-[(2-hydroxyethyl)amino]ethoxy]methyl]-N-(tricyclo[3.3.1.13'7]dec-1-ylmethyl)-benzamide,
2-Chloro-5-[3-[3-(methylamino)propoxy]propyl]-N-(tricyclo[3.3.1.13'7]dec-1-ylmethyl)benzamide,
2-Chloro-5-[3-(3-hydroxy-propylamino)-propoxy]-N-(tricyclo[3.3.1.137]dec-1-ylmethyl)-benzamide,
2-Chloro-5-[2-(3-hydroxypropylamino)ethylamino]-N-(tricyclo[3.3.1.13'7]dec-1-ylmethyl)-benzamide,
2-Chloro-5-[2-(3-hydroxypropylsulfonyl)ethoxy]-N-(tricyclo[3.3.1.13,7]dec-1-ylmethyl)-benzamide,
2-Chloro-5-[2-[2-[(2-hydroxyethyl)amino]ethoxy]ethoxy]-N-(tricyclo[3.3.1.13,7]dec-1-ylmethyl)-benzamide,
2-Chloro-5-[[2-[[2-(1-methyl-1H-imidazol-4-yl)ethyl]amino]ethyl]amino]-N-(tricyclo[3.3.1.13'7]dec-1-ylmethyl)-benzamide,
2-Chloro-5-piperazin-1-ylmethyl-N-(tricyclo[3.3.1.1]dec-1-ylmethyl)-benzamide,
3 7 2-Chloro-5-(4-piperidinyloxy)-N-(tricyclo[3.3.1.1' ]dec-1-ylmethyl)-benzamide,
2-Chloro-5-(255-diazabicyclo[2.2.1]hept-2-ylmethyl)-N-(tricyclo[3.3.1.1]dec-1-ylmethyl)-benzamide,
3 7 2-Chloro-5-(piperidin-4-ylsulfinyl)-N-(tricyclo[3.3.1.1' ]dec-1-ylmethyl)-benzamide,
5-Chloro-2-[3-[(3-hydroxypropyl)amino]propyl]-N-(tricyclo[3.3.1.13,7]dec-1-ylmethyl)-4-pyridinecarboxamide,
2-Chloro-5-[3-[[(1R)-2-hydroxy-1-methylethyl]amino]propyl]-N-(tricyclo[3.3.1.13'7]dec-1-ylmethyl)-3-pyridinecarboxamide,
5-Chloro-2-[3-(ethylamino)propyl]-N-(tricyclo[3.3.1.13'7]dec-1-ylmethyl)-4-pyridinecarboxamide,
5-Chloro-2-[3-[(2-hydroxyethyl)amino]propyl]-N-(tricyclo [3.3.1.13'7]dec-1-ylmethyl)-4-pyridinecarboxamide,
5-Chloro-2-[3-[[(2S)-2-hydroxypropyl]amino]propyl]-N-(tricyclo[3.3.1.13'7]dec-1-ylmethyl)-4-pyridinecarboxamide,
N-[2-Methyl-5-(9-oxa-3,7-diazabicyclo[3.3.1]non-3-ylcarbonyl)phenyl]-tricyclo[3.3.1.137]decane-1-acetamide, or a pharmaceutically acceptable salt or solvate of any one thereof.

In some embodiments, the P2X7 receptor antagonist is selected from the group consisting of

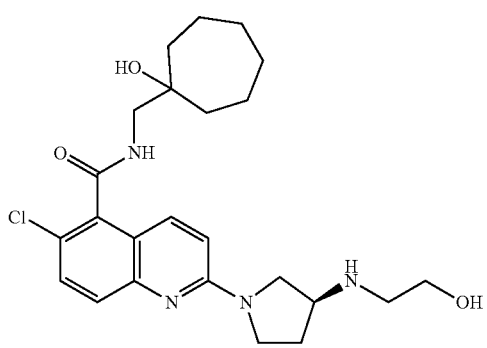

(I)

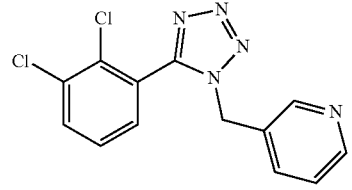

hP2X7 pIC$_{50}$ = 6.9

(17)

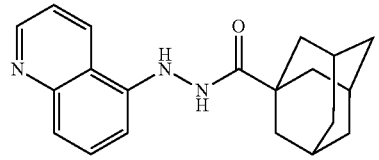

hP2X7 pIC$_{50}$ = 7.99

(18)

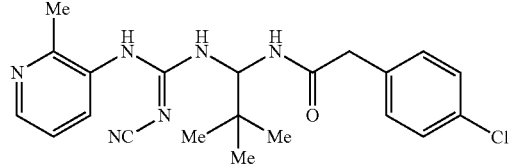

hP2X7 pIC$_{50}$ = 7.5

(19)

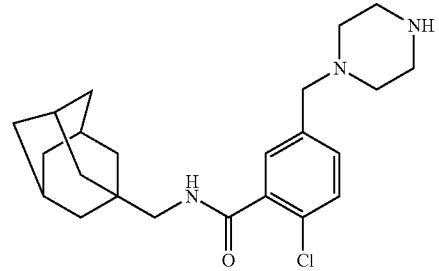

hP2X7 pIC$_{50}$ = 8.0

(20)

In some embodiments, the P2X7 receptor antagonist of the present invention is an antibody having specificity to P2X7.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

In some embodiments, the P2X7 receptor antagonist is an inhibitor of P2X7 receptor expression. An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, anti-sense oligonucleotides, including anti-sense RNA molecules and anti-sense DNA molecules, would act to directly block the translation of P2X7 mRNA by binding thereto and thus preventing protein translation or increasing mRNA degradation, thus decreasing the level of P2X7, and thus activity, in a cell. For example, antisense oligonucleotides of at least about 15 bases and complementary to unique regions of the mRNA transcript sequence encoding P2X7 can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. P2X7 gene expression can be reduced by contacting a subject or cell with a small double stranded RNA (dsRNA), or a vector or construct causing the production of a small double stranded RNA, such that P2X7 gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing P2X7. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

By a "therapeutically effective amount" of the P2X7 receptor antagonist as above described is meant a sufficient amount to provide a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the P2X7 receptor antagonist is employed in conjunction with the administration of one or more anti-retroviral therapeutic compounds. Such compounds include any compound that is useful for inhibiting or destroying retroviruses such as HIV in a patient. Such compounds include, but are not limited to, inhibitors of reverse transcriptase, protease inhibitors, attenuated virus and viral protein vaccines, inhibitors of HIV gene expression, and/or antibodies or synthetic molecules that block CD4 or chemokine receptors. Currently, the most widely used of such compounds include, but are not limited to tenofovir, abacavir, 3TC, FTC, non nucleoside reverse transcriptase inhibitors, integrase and protease inhibitors.

According to the invention, the P2X7 receptor antagonist is administered to the subject in the form of a pharmaceutical composition. Typically, the P2X7 receptor antagonist may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The P2X7 receptor antagonist can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1. Analysis of lymphopoiesis in peripheral blood. (A) Gating strategy to identify recent thymic emigrants, RTEs. (B, C) Percentage of RTEs among CD4+(B) and CD8+(C) T lymphocytes in HIV-uninfected individuals (HIV−, n=5), HIV+ IRs (n=9) and INRs (n=9). Mean values±SEM are presented. The Kruskal-Wallis test was used for comparisons of three groups. NS for P>0.05, *P<0.05, P<0.01. (D) Correlation between RTE frequencies and absolute CD4+ counts. Spearman's rank correlation analysis was performed to determine the slope. **P<0.0001. (E) Percentage of circulating CD34+ cells in the peripheral blood of HIV-uninfected subjects (HIV−, n=18), HIV+ IRs (n=16) and INRs (n=16). Medians are shown. The Kruskal-Wallis test was used for comparisons of three groups, NS for P>0.05. (F) Percentage of $CD38^{low}$ cells among circulating CD34+ cells in some HIV-uninfected subjects (HIV−, n=7), IRs (n=11) and INR (n=6). Medians are shown. The Kruskal-Wallis test was used for comparisons of three groups, NS for P>0.05.

FIG. 2. Limiting dilution assays (LDAs) to determine the T-cell and B-cell differentiation potential of CD34+ cells. (A) LDA design. Conditions for determining T-cell potential a and B-cell potential$^b$ are shown. For further details, see the materials and methods. (B, C) Examples of positive wells on D21, for cell cultures of T-cell precursors (B) defined as $CD45RA^{high}CD7+CD5+CD1a+$ cells, and B-cells (C) defined as $CD79a^{intra+}$ cells. (D) Analysis of the T-cell potential of CD34+ cells. Each point on the graph represents the mean value from three independent experiments. (E) The presence of T-cell and B-cell precursors was assessed with the ELDA webtool, by application of the maximum likelihood method to the Poisson model. Mean values (min-max) for three experiments are indicated for each group and set of conditions. NS for P>0.05, P<0.01, *P<0.001.

FIG. 3. Analysis of IL7R polymorphisms and Notch activation in CD34+ cells from IRs and INRs. (A) IL7RA polymorphisms in HIV-infected patients. The allelic frequency of each SNP is shown. Fisher's exact test was used to compare the distribution of SNPs between IRs (n=9) and INRs (n=10). NS for P>0.05. (B) Expression of the Notch target gene HES1 in purified CD34+ cells from HIV-uninfected subjects (n>3), IRs (n=4) and INRs (n=6) exposed overnight to IgG1-Fc (IgG), Delta-like 4 (DLL-4), and DLL-4 and hIL-7 (DLL-4+IL7) (5 μg/mL for DLL-4 and 5 ng/mL for IL-7). Means and the standard error of the mean are shown. The Kruskal-Wallis and Friedman tests were used to compare differences in mRNA levels between groups, for each set of conditions (unpaired data), and between sets of conditions for the same group (paired data), respectively. *P<0.05, **P<0.01.

Figure 4:
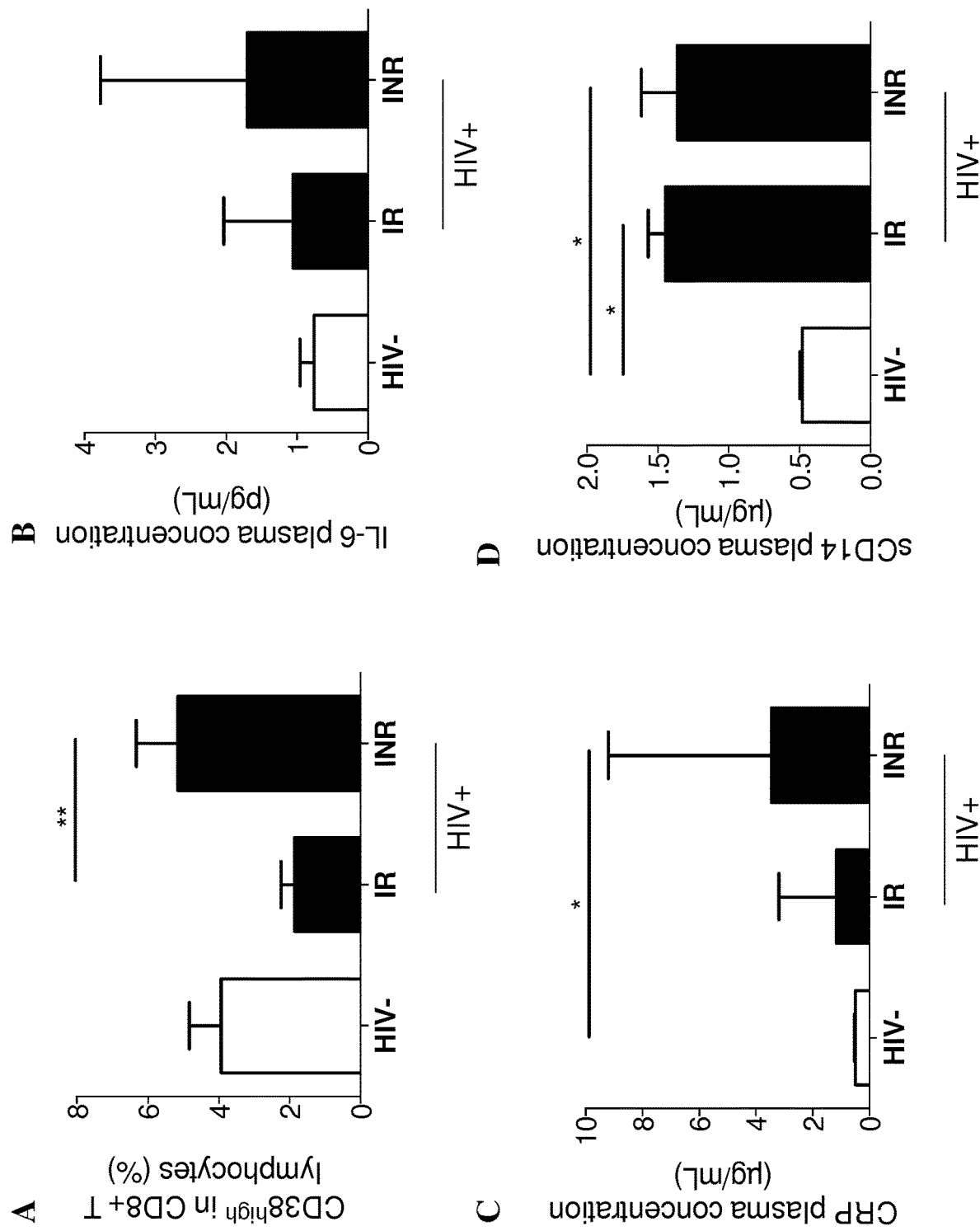

FIG. 4. Immune activation and inflammation in HIV-uninfected individuals and HIV-infected patients. (A) Percentage of $CD38^{high}$ cells among CD8+T lymphocytes (HIV−, n=18; IRs, n=16; INRs, n=16). (B, C, D) Plasma concentrations of IL-6 (B), CRP (C) and sCD14 (D) in HIV-uninfected (HIV−, n=3) and HIV-positive individuals (IRs, n=15; INRs, n=16). Bars indicate the means and the standard error of the mean. The Kruskal-Wallis test was used to determine differences between groups. NS for P>0.05, *P<0.05, **P<0.01.

FIG. 5. Molecular analysis of cell death pathways in CD34+ cells. (A, B, C) RT-qPCR analysis in ex vivo purified CD34+ cells of FAS (A), P2X7 (B) and CD73 (C) mRNA levels (HIV−, n=6; HIV-positive IRs, n=5; HIV-positive INRs, n=4). Means and standard errors are shown. The Kruskal-Wallis test was used to determine differences between groups. NS for P>0.05, *P<0.05. (D) Limiting dilution assay, as described in FIG. 2, for T-cell potential, performed with CD34+ cells from HIV-positive INRs in T-cell medium alone (mock) or in T-cell medium supplemented with 20 μM PPAD. Mean (min-max) values for three patients are shown. The ELDA webtool was used to generate the results. *P<0.05.

Figure 6:
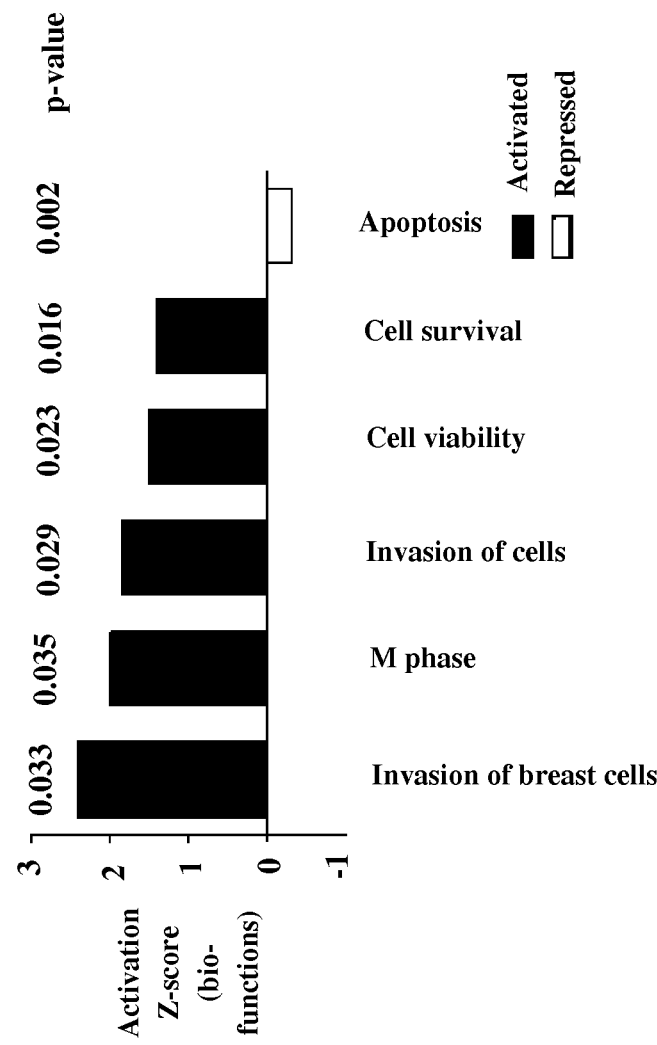

FIG. 6. Transcriptomic analysis of CD34+ cells in HIV-infected IRs and INRs. The top 5 biological functions in Ingenuity® analysis, based on activation z-score, an algorithm predicting whether the genes of the group are in an activated or inactivated state. Rank in the top 5 is indicated by the number after the #. P-values are shown. Biological functions upregulated (positive z-score) in IR patients are shown in red, and biological functions downregulated in IR patients (negative z-score) are shown in green.

EXAMPLE

Material & Methods

Patient Samples

Peripheral blood samples were collected from HIV-negative healthy donors at the Centre regional de transfusion sanguine and from HIV+ patients on c-ART followed at Henri Mondor Hospital (Créteil, France). Ethics committee approval and written informed consent from the subjects included were obtained, in accordance with the Helsinki Declaration, prior to study initiation.

Flow Cytometry Analyses

We used the following conjugated antibodies: CD38-fluorescein isothiocyanate, CD34-phycoerythrin (PE)-cyanin5 (Cy5), CD4-Pacific Blue, CD19-allophycocyanin (APC), CD3-Alexa Fluor 700, CD8-APC-H7, CCR7-Alexa Fluor 647, CD79a-APC from BD Biosciences (San Jose, Calif.); CD56-PE, CD45RA-PE-TexasRed, CD7-PE-Cy7, CD1a-PE, CD5-PE-Cy5 from Beckman Coulter (Brea, Calif.); CD31-PE from Miltenyi Biotech (Bergisch Gladbach, Germany) and CD27-PE-Cy7 from eBioscience (San Diego, Calif.). We obtained LIVE/DEAD aqua fluorescent dye from Molecular Probes (Invitrogen, Carlsbad, Calif.). The Fam-FLICA-FITC probe against active caspase-1 was used according to the manufacturers' instructions (ImmunoChemistry, Bloomington, Minn.). Standard protocols were used for all types of staining. Samples were acquired on an LSRII Flow Cytometer (BB Biosciences), and the data were analyzed with FlowJo v7.6.5 (Treestar, Ashland, Oreg.).

Quantification of HIV-1 DNA and Inflammation Factors

Cell-associated HIV DNA was quantified by ultrasensitive real-time PCR (Biosentric, Bandol, France), in total PBMCs, as previously described (41). Plasma samples were used to determine the concentrations of IL6, CRP and sCD14 with Quantikine ELISA kits (R&D Systems, Minneapolis, Minn.) according to the manufacturer's protocol.

Limiting Dilution Assay (LDA) for Determining the T- and B-Cell Potentials of Circulating CD34+ Cells PBMCs were separated using Ficoll-Hypaque (PAA, Pasching, Austria). The CD34+ cells were subjected to immunomagnetic sorting with a Diamond CD34 Isolation Kit, according to the manufacturer's instructions (Miltenyi Biotech). The enriched population had a purity >95%. We plated various numbers (10, 20, 50) of CD34+ cells on a layer of OP9-DLL1 stromal cells in the presence of 5 ng/mL hFlt3L and 5 ng/mL hIL-7 (R&D Systems) for T-cell development, or on MS5 stromal cells in the presence of IL-2 (10 ng/mL), IL-15 (1 ng/mL) and SCF (50 ng/mL) (Miltenyi Biotech) for B-cell development, as previously described(47). When specified, the P2X7 antagonist pyridoxal-phosphate-6-azophenyl-2'-4'disulfonate (PPAD) was added to the medium (20 µM, Sigma-Aldrich, St. Louis, Mo.). For limiting dilution assays, the cells were cultured for 21 days, then collected and analyzed for the presence of T-cell (CD45RA+ CD7+CD5+CD1a+) or B-cell (CD79a$^{intra}$) precursors. The frequency of T- and B-cell precursors was calculated with the ELDA webtool, by applying the maximum likelihood method to the Poisson model (47).

Molecular Analysis of mRNA Levels

Purified CD34+ cells were exposed overnight to IgG1-Fc or DLL4-Fc (5 µg/mL, generously provided by A. Sakano (98)) in T-cell medium with or without IL-7, as previously described (45-47, 79). RNA was isolated in TRIzol (Invitrogen), according to the standard procedure. RT-qPCR was carried out with the SuperScript VILO™ cDNA synthesis kit (Invitrogen) and Brilliant II SYBR Green Master Mix (Agilent, Santa Clara, Calif.), in standard conditions, on an MX3005P (Stratagene, La Jolla, Calif.). The primer sequences used have been described elsewhere (79).

DNA Extraction and Sequencing

Total DNA was extracted from PBMCs collected from HIV-infected IRs and INRs, with the DNeasy Blood and Tissue Kit (Qiagen, Hilden, Germany), used according to the manufacturer's protocol. PCR was performed with the Platinum Taq DNA Polymerase High Fidelity (Invitrogen), in standard conditions, on a 2720 Thermal Cycler (Applied Biosystems, Carlsbad, Calif.). The primers used to target SNPs were as follows: IL7RA-1 (3994-4281), IL7RA-2 (23356-23652), IL7RA-3 (25664-25969), and IL7RA-4 (22516-22811). The PCR products were sequenced in both directions with the BigDye® Terminator v3.1 Sequencing Kit (Applied Biosystems) and processed on an automated sequencer (ABI PRISM® 3130XL Genetic Analyzer, Applied Biosystems). Chromatograms were analyzed with Chromas (Technelysium, South Brisbane, Australia) and ClustalW (EMBL-EBI, Heidelberg, Germany).

Microarray Analysis

RNA was extracted from ex vivo purified CD34+ cells with the RNeasy Micro Kit (Qiagen), and quantified on an ND-8000 spectrophotometer (NanoDrop Technologies, Wilmington, Del.). Its integrity was then checked on a 2100 BioAnalyzer (Agilent Technologies). In vitro transcription was performed on 60 ng of RNA (Ambion Illumina TotalPrep RNA Amplification Kits, Applied Biosystems/Ambion), as described elsewhere(99).

Statistical Analysis

All statistical analyses were performed with GraphPad Prism software v6 (La Jolla, Calif.). We used nonparametric Mann-Whitney and Kruskal-Wallis tests to compare continuous variables between two and three groups, respectively. For paired groups, Wilcoxon tests were used. Discrete variables were compared in Fisher's exact tests. Differences were considered non-significant if P>0.05. Microarray data were analyzed by ViroScan3d (Lyon, France), as previously described (99). Ingenuity pathway analysis (Qiagen) was also conducted, focusing on both canonical pathways and biological functions.

Results

Enrollment and Characteristics of the Patients

We selected from our cohort of HIV+ patients, those with poor immunological CD4+ T-cell restoration (i.e. CD4+ T-cell count <500/mm$^3$ and a CD4/CD8 ratio <1), with an undetectable plasma viral load for more than eight years. These patients are referred to hereafter as "immunological non-responders" (INRs). Patients with high levels of immunological CD4+ T-cell recovery (i.e. with values close to those of the general population of uninfected individuals: >900 CD4+ T-cells/mm$^3$ and a CD4/CD8 ratio >1 (40)), referred to hereafter as "immunological responders" (IR) were selected and matched with INRs for predictive parameters of immune recovery on c-ART, including estimated date of infection, treatment duration, periods with a sustained undetectable viral load (i.e. <50 HIV-1 RNA copies/mL), CD4+ nadir and pre-therapy CD4+ counts (Table 1). HIV-uninfected individuals were matched with HIV-positive patients for age. Median (IQR) absolute CD4+ T-cell counts were, as expected, higher in HIV-positive IRs (1086 cells/mm$^3$ (927-1194)) than in INRs (379.5 cells/mm$^3$ (280.3-431), P<0.0001), but median absolute CD8+ counts did not differ between these two subsets of patients (644.5 cells/mm$^3$ (568.5-798.5) for IRs and 621 cells/mm$^3$ (492.5-808.8), P=NS) for INRs). We also assessed the viral reservoir, by measuring cell-associated HIV-1 DNA levels in peripheral blood mononuclear cells. IRs and INRs presented similar HIV-1 DNA levels (3.25 log$_{10}$ HIV-1 DNA copies/mL (2.65-3.4) and 3.15 (2.75-3.36), respectively (P=NS)).

TABLE 1

Characteristics of subjects included in the study.

| | | | | P | | |
|---|---|---|---|---|---|---|
| Characteristic | HIV− | HIV+ IR | HIV+ INR | HIV− vs IR | HIV− vs INR | IR vs INR |
| Number | 18 | 16 | 16 | | | |
| Age (year) | 47.5 (34-55.25) | 46 (40.25-52.75) | 53 (47-63) | NS | NS | NS |
| Sex ratio, F/M | 0.21 | 0.5 | 0.8 | NS | NS | NS |
| Ethnic origin, % | | | | | | |
| Caucasian | NA | 68.75 | 62.5 | | | NS |
| African | NA | 31.25 | 37.5 | | | NS |
| Infection duration (years) | — | 10 (7.5-18.75) | 13 (8-17) | | | NS |

TABLE 1-continued

Characteristics of subjects included in the study.

| | | | | P | | |
|---|---|---|---|---|---|---|
| Characteristic | HIV– | HIV+ IR | HIV+ INR | HIV– vs IR | IR vs INR | HIV– vs INR |
| Treatment duration (years) | — | 9.5 (7.25-14.75) | 13 (8-16) | | NS | |
| Time of indetectable VL (years)$^a$ | — | 11 (8.25-16.75) | 12 (9-15) | | NS | |
| CD4 nadir (cells/mm$^3$) | — | 191 (103-261) | 102 (48-197) | | NS | |
| VL baseline (copies/mL)$^b$ | — | 81040 (25529-500000) | 46571 (16809-259102) | | NS | |
| CD4 baseline (cells/mm$^3$)$^b$ | — | 225 (150-305) | 191.5 (59.75-243.5) | | NS | |
| CD4 absolute count (cells/mm$^3$)$^a$ | NA | 1086 (927-1194) | 379.5 (280.3-431) | | **** | |
| CD4, %$^a$ | 49.13 (45.09-55.07) | 41.85 (37.72-50.71) | 27.46 (20.16-37.14) | * | *** | **** |
| CD8 absolute count (cells/mm$^3$)$^a$ | NA | 644.5 (568.5-798.5) | 621 (492.5-808.8) | | NS | |
| CD8, %$^a$ | 19.85 (17.46-26.09) | 23.64 (20.85-26.63) | 36.82 (30.55-48.82) | NS | **** | **** |
| CD4/CD8 ratio$^a$ | 2.31 (1.8-3.02) | 1.69 (1.39-1.86) | 0.58 (0.48-0.77) | *** | **** | **** |
| HIV Reservoir (log$_{10}$ HIV DNA copies/mL of plasma)$^{a,c}$ | — | 3.25 (2.65-3.4) | 3.15 (2.75-3.36) | | NS | |

$^a$on entry into the study;
$^b$at the time of c-ART initiation;
$^c$HIV-1 2-LTR circles were quantified with primers spanning the 2-LTR circle junction, as previously described (41, 42). Real-time PCR was performed in triplicate on each sample.
HIV– = HIV-uninfected subjects;
IR = immunological responders;
INR = immunological non-responders;
F = female;
M = male;
NA = not available.
Medians (IQR) are shown. The Mann-Whitney and Kruskal-Wallis tests were used to compare two and three groups, respectively. Fisher's exact test was used to compare sex ratios and ethnic origins.
NS for P > 0.05, * P < 0.05, * P < 0.001, ** P < 0.0001.

Impaired T-Cell Lymphopoiesis in INRs

We analyzed the frequency of recent thymic emigrants (RTEs), defined as CD31$^{high}$CD27+CCR7+CD45RA+ CD4+ and CD8+ cells in our three groups of subjects (FIG. 1A). The percentages of RTEs among CD4+ and CD8+ cells did not differ between HIV-uninfected individuals and IRs (28% (24.75-33.35) and 24.3% (16.7-29.05) for CD4+, and 37.9% (31.15-43) and 37.6% (17.45-60.6) for CD8+ RTEs, respectively, P=NS for both comparisons) (FIG. 1B, C). By contrast, the frequency of CD4+(8.61% (5.46-17.65)) and CD8+(13.7% (5.01-21.75)) RTE cells was markedly lower in INRs than in HIV-uninfected subjects (P<0.01 and P<0.05, respectively) and IRs, P<0.05 for both comparisons). The frequency of CD4+ RTEs was correlated with peripheral CD4+ count (FIG. 1D, P<0.0001).

Levels of T-cell production may be low due to less efficient seeding of the thymus by CD34+ cells. We therefore determined the frequency of CD34+ cells in peripheral blood. We found no difference in the frequency of these cells between the three groups (HIV-uninfected, 0.071% (0.0345-0.1395); IRs, 0.053% (0.0285-0.1085) and INRs, 0.0650% (0.03325-0.1415)), overall P=NS) (FIG. 1E). Moreover, the frequency of blood CD34+CD38$^{low}$ immature progenitors was similar in HIV-uninfected individuals (68.43 (17-81)), IRs (69.64 (22.77-84.21)) and INRs (51.27 (36.16-66.67), overall P=NS) (FIG. 1F). Thus, INRs present impaired T-cell lymphopoiesis but have similar levels of circulating progenitors to IRs or HIV-uninfected subjects.

Alteration of T-Cell Differentiation Potential of CD34+ Cells is Associated with Poor CD4+ Recovery We then investigated whether the lower thymic output of INRs was due to functional alterations of CD34+ cells. We assessed the lymphoid potential of circulating CD34+ cells in LDA (FIG. 2A, B, D). The T-cell potential of the CD34+ cells from IRs did not differ from that of HIV-uninfected individuals (1/86.3 (1/67.3-1/111) vs. 1/71.9 (1/54.8-1/94.5), P=NS) (FIG. 2E). By contrast, this potential was much lower in INRs (1/240.6 (1/162.1-1/806.6)) than in either HIV-uninfected subjects (P<0.01) or IRs (P<0.001). We then investigated whether this alteration in the lymphoid potential of the CD34+ cells was specific to the T-cell lineage. We performed LDAs in B-cell conditions (FIG. 2A, C, E). We found no difference in the B-cell potential of CD34+ from HIV-uninfected subjects (1/63.1 (1/42.5-1/94.1)), IRs (1/47 (1/32.5-1/68.2)) and INRs (1/64 (1/42.04-1/100.1), overall P=NS). T-cell potential was inversely correlated with peripheral CD4+ T-cell counts and percentages in the patients studied. Our results demonstrate that the T-cell differentiation potential of CD34+ cells is specifically altered in INRs and that this alteration is associated with poor CD4+ T-cell recovery on c-ART.

The Impaired Differentiation of T-Cells from CD34+ Cells in INRs is not Associated with Altered Responses to Notch or a Particular Genotype of IL7RA The IL7/IL7R and Notch pathways are the two principal pathways of T-cell differentiation (43-47). We therefore investigated whether perturbations to these two pathways could account for the lower T-cell potential of CD34+ cells in INRs. We assessed the prevalence in our patients of SNPs in the IL7R gene associated with decreases in T-cell production: SNPs present in the promoter region (rs7701176), exon 6 (rs6897932), intron 6 (rs987106) and 3' region (rs10491434) (15) (FIG. 3A). There was no clear difference in the distribution of polymorphisms between the two groups of HIV-infected patients. Moreover, sIL7RA (soluble) and mIL7RA (membrane-bound) mRNA levels were similar between HIV-uninfected individuals and HIV-infected patients in studies on ex vivo purified CD34+ cells (data not shown). NOTCH1 mRNA levels were also similar in subjects with and without HIV infection (data not shown). We assessed the functionality of the Notch1 receptor by analyzing the expression of Notch target genes in CD34+ cells after incubation with a recombinant Notch ligand, Delta-like 4 (hDLL4-Fc), in the presence of IL-7 (45). HES' mRNA levels increased rapidly after incubation with DLL4 or with DLL4 plus IL-7, in cells from HIV-uninfected and HIV-infected individuals (FIG. 3B, P<0.05). However, no difference in the expression of HES' and other Notch reporter genes (IL7R, NOTCH3, data not shown) was observed between IRs and INRs. These results suggest that alterations in Notch signaling and IL7RA genetic background cannot account for the impaired lymphopoiesis in INRs.

Persistent Immune Activation and Inflammation in Immunological Nonresponders

Previous studies have shown that chronic immune activation and inflammation affect immune restoration in patients on c-ART (9-12, 48). An analysis of the frequency of CD8+CD38+ T-cells revealed very low levels of T-cell activation (1.25% (0.9863-2.755)) in IRs, similar to that in HIV-uninfected subjects (2.013% (1.452-6.6898), P=NS) (FIG. 4A). INRs had a higher percentage of CD8+CD38+ T-cells than IRs (3.638% (2.509-7.28) (P<0.01). However, CD8+CD38+ T-cell frequency in these patients was not correlated with CD4+ T-cell counts or with CD4+ RTEs in the peripheral blood (P=NS). Plasma IL-6 concentration was similar between HIV-uninfected subjects (0.76 pg/mL (0-0.96)) and IRs (1.06 pg/mL (0.56-2.04)), but tended to be slightly higher in INRs (1.7 pg/mL (1.01-3.78), overall P=NS) (FIG. 4B). Consistent with this observation, plasma CRP levels in INRs (3.45 µg/mL (0.58-9.21)) were higher than those in HIV-uninfected individuals (0.5 µg/mL (0.07-0.54), P<0.05), but not significantly different from those in IRs (1.16 µg/mL (0.75-3.19), P=NS) (FIG. 4C). Both IRs and INRs had higher plasma concentration of sCD14 (1.45 µg/mL (1.36-1.57) for IRs and 1.37 µg/mL (1.19-1.62) for INRs, P=NS)) than HIV-uninfected subjects (0.48 µg/mL (0.33-0.5), P<0.05) (FIG. 4D). However, none of the studied soluble markers was positively correlated with peripheral CD4+ T-cell count in IRs and INRs. Thus, overall, the data presented indicate that INRs present persistent immune activation and inflammation despite virologically successful long-term c-ART.

Figures 5A, 5B:
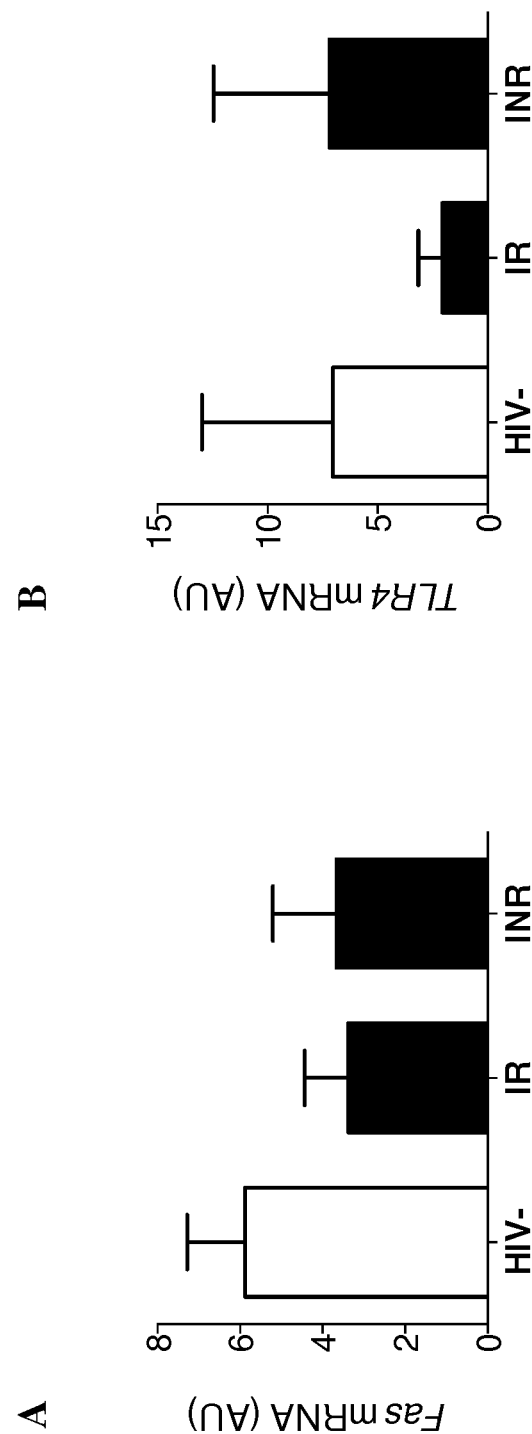
Figures 5C, 5D:
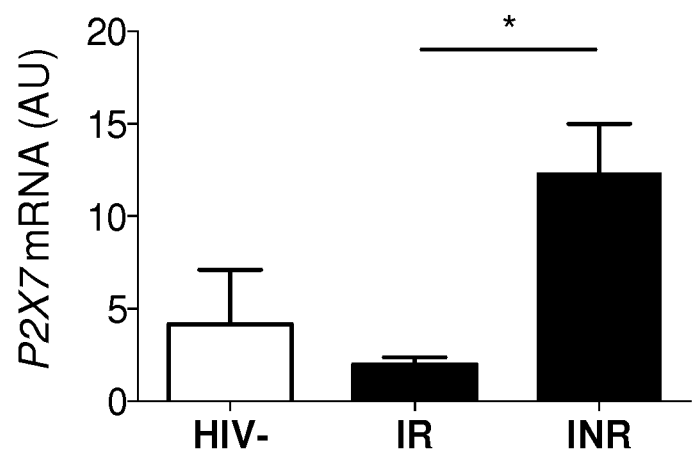

P2X7 Expression is Strongly Expressed on CD34+ Cells in INRs and its Inhibition Restores the Potential for T-Cell Differentiation We then asked whether the impaired differentiation of CD34+ cells into T-cells resulted from changes in death pathways due to persistent immune activation in INRs. We observed no difference in the FAS expression of CD34+ cells between HIV-uninfected subjects and HIV-infected IRs and INRs (FIG. 5A, P=NS). Extracellular nucleotides and purinergic receptors modulate CD34+ homeostasis (49-53). The binding of ATP to its receptor P2X7 induces the assembly of a cytoplasmic multipartner complex, the inflammasome, and caspase-1 activation, leading to secretion of the proinflammatory cytokines, IL1ß and IL-18 (54, 55). We observed no difference in caspase-1 activation in ex vivo circulating CD34+ cells between the different groups of subjects (data not shown), but P2X7 was found to be markedly upregulated in INRs, in comparisons with IRs and HIV-uninfected subjects (FIG. 5B, P<0.05). Extracellular ATP may also be hydrolyzed by the ectoenzymes CD39/CD73 (56-61). CD39 expression was similar between HIV-uninfected and infected IR and INR individuals (data not shown), but CD73 expression was undetectable in all the INRs studied (FIG. 5C, P<0.05).

We investigated the role of P2X7 in poor immune restoration in HIV patients, in LDAs involving irreversible antagonism with PPAD. We showed that P2X7 inhibition significantly improved the T-cell differentiation potential of CD34+ cells from INRs (1/145.3 (1/98.3-1/214.7) in the presence of PPAD vs. 1/314.7 (1/186.3-1/532.3) in its absence, P<0.05)) (FIG. 5D). The longitudinal follow-up of inflammation markers for up to four years in 15 HIV-positive patients showed no correlation with P2X7 expression on CD34+ cells (Figure S3A-F). These results suggest that abnormally high levels of P2X7 expression and an absence of CD73 affect the normal differentiation of CD34+ cells into T-cells in INRs, probably by increasing the susceptibility of these cells to extracellular ATP.

Microarray Analysis Reveals a Downregulation of Cell Survival Pathways and an Upregulation of Apoptosis in CD34+ Cells from INRs We explored the mechanisms underlying the functional alterations of CD34+ cells in INRs, by performing transcriptomic analysis in ex vivo-purified CD34+ cells from IRs and INRs (data not shown). The gene expression profiles of these two groups were very similar, with only 210 genes differentially expressed. These genes were grouped by biological function, with identification of the top five on the basis of activation z-score (FIG. 6B). This score predicts the activated (positive z-score) or inactivated (negative z-score) state of genes from the same functional group. Cells from IR patients displayed upregulation for genes from the following categories: mitosis M phase (PKP4 (FC=7,919), SEPT11 (FC=2,469)), cell viability (DEF6 (FC=1,64), GADD45B (FC=1,752)) and survival (PRKCZ (FC=3,104), RFC1 (FC=2,090)). In IRs, a negative z-score was attributed to apoptosis (RNASEL (FC=6,642), BIRC2 (FC=2,375), IFIH1 (FC=1,939), P<0.01). Gene expression profile analysis revealed a role for general mechanisms of cell survival and death in CD34+ cells from INRs. The observed differences may underlie the low T-cell potential and poor CD4+ T-cell recovery.

DISCUSSION

This study provides insight into the major mechanisms driving immune recovery in HIV-infected patients on long-term virologically successful c-ART regimens. The design of this study differs from those of most studies concerning poor immune recovery. First, we selected patients with opposite and extreme immunological profiles. Second, the patients enrolled in this study had been treated for at least eight years, and for up to sixteen years in some cases, whereas most previous studies were carried out two to four years after c-ART initiation (4, 40, 62-65) and only a few investigated immune recovery mechanisms after more than five years of treatment (6, 66-68). Finally, we applied strict criteria for patient selection and most of the parameters predictive of immune recovery described in previous studies were characterized in our patients (age (3-5), sex (5, 69), and ethnic origin (69), durations of infection and treatment, duration of undetectable viral load period, nadir and pre-therapy CD4+ counts (4, 6-8)).

Low levels of de novo lymphocyte production in HIV+ individuals and peripheral dysfunction are considered to be major barriers to efficient immune restoration (65, 70-74). We showed, by assessing CD4+ and CD8+ RTE frequencies, that lymphopoiesis was severely compromised in INRs. Our results provide strong evidence that T-cell recovery is influenced by the impairment of CD34+ cells. Like Mendez-Lagares et al. (64) and Baillou et al. (28), but unlike Sauce et al. (34), we found no difference in peripheral CD34+ cell frequency between HIV-uninfected subjects, IRs and INRs. We also observed no decrease in the frequency of precursors already committed to T-cell development in IRs (data not shown).

Finally, circulating CD34+ cells from INRs displayed functional alterations, with a specific decrease in T-cell precursor differentiation. Several studies have already described a suppression of hematopoiesis in HIV-infected individuals (17, 20, 25, 27-35) and experimental animal models (26, 36-38), but only a few focused on T-cell development during HIV infection (30, 31, 34, 37-39). Using an indirect technique involving the use of surface markers expressed on circulating CD34+ cells to determine the lymphoid/myeloid ratio, one team concluded that changes in lymphoid potential might be characteristic of HIV infection (34). FTOC assays, a more appropriate analysis of T-cell development, revealed a decrease in immature (CD4+CD8+CD3-) and mature (CD4+CD8+CD3+) T-cell generation from blood CD34+ HPCs, regardless of the level of T-cell restoration (30, 31, 38). However, FTOC provides no information about the frequency of T-cell precursors and cannot be used to quantify T-cell development. It may also be biased by the presence of mature contaminants. A similar impairment of hematopoiesis has been described in SIV infection (26, 36-38). We cannot exclude the possibility that CD34+ cells from INRs display impaired differentiation into other hematopoietic lineages. However, we did not observe differences in B-cell generation. Furthermore, we found that the T-cell potential of CD34+ progenitors was strongly correlated with the degree of peripheral T-cell restoration, implying that the maintenance of adequate lymphocyte levels is highly dependent on efficient de novo T-cell lymphopoiesis.

Regardless of the population studied, some authors have suggested that CD34+ cells or more differentiated colonies may be directly infected (26, 28, 30, 36), although the evidence for this is minimal. Several viral proteins (gp120 (75) or Nef (76)) have been shown to impair CD34+ differentiation. We performed HIV RNA quantification on culture supernatants, but detected no ongoing viral replication (data not shown). We cannot rule out the possibility of latent infection, but the incidence of such infection would be too low to account for such specific changes in T-cell differentiation.

We investigated the molecular abnormalities underlying impaired lymphopoiesis, focusing in particular on the key factors for T-cell lymphopoiesis, Notch and IL7R. Some IL7RA SNPs have been reported to be associated with impaired immune recovery (14, 77, 78), but the prevalence of these SNPs was not higher in INRs and no differences were found in mRNA levels for soluble and membrane-bound IL7R. Target gene expression was similar in INRs and HIV-uninfected subjects following a short period of Notch activation. However, the timing of the transcriptional programs downstream from Notch signaling is highly variable (79). We therefore cannot exclude the possibility that some differences in the response to Notch ligands become visible only after longer periods of stimulation, although this would be difficult to test because survival issues affect mRNA quality at later time points in feeder cell-free culture systems.

Consistent with previous reports, we observed abnormal immune activation in INRs despite long-term c-ART. We also found that sCD14 levels remained high in treated HIV patients, as reported in a previous study (80). Analyses of plasma samples collected from the HIV patients over the last few years showed that the levels of soluble markers of inflammation remained stable and high over time. The observed inflammation would probably affect CD34+ cell survival. The Fas receptor did not seem to be involved in this process. We therefore investigated other cell death pathways involving ATP signaling. The availability of extracellular ATP is regulated by the CD39/CD73 ectoenzymes (56-61). In the absence of ectonucleotidase activity, high ATP concentrations trigger the low-affinity P2X7 receptor to induce the massive release of proinflammatory cytokines and cell death by pyroptosis (81). We provide several lines of evidence suggesting that T-cell differentiation is impaired due to the extremely high sensitivity of CD34+ HPCs to extracellular nucleotides. CD34+ cells displayed P2X7 upregulation and no CD73 expression in CD34+ cells from INRs, suggesting that these cells are more prone to ATP-induced cell death. Consistent with this hypothesis, a P2X7 antagonist restored the T-cell differentiation of CD34+ cells in INRs. ATP has been reported to be involved in stem cell metabolism (49-53). In murine hematopoietic and human neural progenitors, extracellular ATP causes rapid cell death and an increase in apoptotic features (53, 82). It is spontaneously released in cultures of human mesenchymal stem cells, inhibiting cell proliferation, and it appears to be key regulator of early lineage commitment (83, 84). Consistently, transcriptomic analysis revealed that CD34+ cells from IRs underwent mitosis, unlike the non-cycling cells of INRs. The greater immune activation observed in the peripheral blood of INRs may also occur in the bone marrow. IL-6 and sCD14 are markers of monocyte/macrophage activation, principal supporting cells of the bone marrow niche. LPS, through sCD14, may trigger TLR4-promoted cell death and initiate an auto-amplification loop in which dying cells release their content, thereby creating a highly inflammatory environment for neighboring differentiating progenitors. In this setting, other P2X7-expressing cells may also contribute to the chronic inflammatory state. We did not observe altered caspase-1 activation profile in ex vivo studied hematopoietic progenitors, suggesting that there was no ongoing pyroptosis. However, further studies are undoubtedly required to define the precise mechanism of CD34+ cell turnover in inflammatory conditions.

Also, it is unclear why B-cell differentiation is intact. One explanation could be the role of IL7 in this process. First, B-cell lymphopoiesis in humans does not rely on IL7 in contrast to mice (85-87). Second, we previously demonstrated that transcriptional expression of P2X7 is increased by IL7 (88). Even if we did not measure plasma IL7 levels, they are likely to be elevated in INR, as a cause or a consequence of low CD4 T-cell levels. We postulate that at early stages of lymphopoiesis IL7 potentiates the extracellular nucleotide signaling, which could induce cell death and be important regulator of stem cells metabolism. At late stages, expansion of maturating progenitors is highly depending on IL7 (45). This would reflect its dual role in T-cell development.

Finally, microarray comparisons of IRs and INRs revealed that CD34+ cells from INRs lacked proliferation- and survival-associated transcripts. The mRNAs for PKP4 and SEPT11, involved in cytokinesis during cell division (89, 90), PRKCZ, an important target of PI3K signaling (91), DEF6, regulating lymphocyte survival (92), and GADD45B, involved in FOXO signaling, oxidative stress resistance and DNA repair (93), were also downregulated. Conversely, these cells displayed an upregulation of genes involved in cell death, such as RNASEL and BIRC2 (encoding cellular inhibitor of apoptosis, cIAP) (94, 95). Further characterization of the genes identified in microarray analyses should help us to determine which factors limit the differentiation of CD34 HPCs from INRs into T cells.

Our findings suggest that patients with limited immune recovery on c-ART could be treated with complementary strategies, such as anti-inflammatory compounds and, more specifically, P2X7 inhibitors (96), which have been shown to have a good safety profile in clinical trials (97).

These findings provide compelling evidence that successful immune restoration in HIV-infected patients on c-ART involves the regeneration of new T-cells from CD34+ cells. It may therefore be possible to identify potential targets for the enhancement of T-cell lymphopoiesis in patients with an incomplete restoration of CD4 T-cell counts on c-ART.

REFERENCES

Throughout this application, various references describe the state of the art to which this invention pertains. The disclosures of these references are hereby incorporated by reference into the present disclosure.

1. Lewden C, Chene G, Morlat P, Raffi F, Dupon M, Dellamonica P, et al. HIV-infected adults with a CD4 cell count greater than 500 cells/mm3 on long-term combination antiretroviral therapy reach same mortality rates as the general population. Journal of acquired immune deficiency syndromes (1999). 2007; 46(1):72-7.
2. Costagliola D, Lacombe J M, Ghosn J, Delaugerre C, Pialoux G, Cuzin L, et al. CD4+ cell count recovery in naive patients initiating cART, who achieved and maintained plasma HIV-RNA suppression. J Int AIDS Soc. 2014; 17(4 Suppl 3):19481.
3. Appay V, Fastenackels S, Katlama C, Ait-Mohand H, Schneider L, Guihot A, et al. Old age and anti-cytomegalovirus immunity are associated with altered T-cell reconstitution in HIV-1-infected patients. AIDS. 2011; 25 (15): 1813-22.
4. Hunt P W, Deeks S G, Rodriguez B, Valdez H, Shade S B, Abrams D I, et al. Continued CD4 cell count increases in HIV-infected adults experiencing 4 years of viral suppression on antiretroviral therapy. AIDS. 2003; 17(13):1907-15.
5. Gandhi R T, Spritzler J, Chan E, Asmuth D M, Rodriguez B, Merigan T C, et al. Effect of baseline- and treatment-related factors on immunologic recovery after initiation of antiretroviral therapy in HIV-1-positive subjects: results from ACTG 384. Journal of acquired immune deficiency syndromes (1999). 2006; 42(4):426-34.
6. Moore R D, Keruly J C. CD4+ cell count 6 years after commencement of highly active antiretroviral therapy in persons with sustained virologic suppression. Clinical infectious diseases: an official publication of the Infectious Diseases Society of America. 2007; 44(3):441-6.
7. Kaufmann G R, Furrer H, Ledergerber B, Perrin L, Opravil M, Vernazza P, et al. Characteristics, determinants, and clinical relevance of CD4 T cell recovery to <500 cells/microL in HIV type 1-infected individuals receiving potent antiretroviral therapy. Clinical infectious diseases: an official publication of the Infectious Diseases Society of America. 2005; 41(3):361-72.
8. Guihot A, Tubiana R, Breton G, Marcelin A G, Samri A, Assoumou L, et al. Immune and virological benefits of 10 years of permanent viral control with antiretroviral therapy. AIDS. 2010; 24(4):614-7.
9. Deeks S G, Kitchen C M, Liu L, Guo H, Gascon R, Narvaez A B, et al. Immune activation set point during early HIV infection predicts subsequent CD4+ T-cell changes independent of viral load. Blood. 2004; 104(4): 942-7.
10. Hunt P W, Martin J N, Sinclair E, Bredt B, Hagos E, Lampiris H, et al. T cell activation is associated with lower CD4+ T cell gains in human immunodeficiency virus-infected patients with sustained viral suppression during antiretroviral therapy. The Journal of infectious diseases. 2003; 187(10):1534-43.
11. Sandler N G, Sereti I. Can early therapy reduce inflammation? Current opinion in HIV and AIDS. 2014; 9(1): 72-9.
12. Wilson E M, Singh A, Hullsiek K H, Gibson D, Henry W K, Lichtenstein K, et al. Monocyte-activation phenotypes are associated with biomarkers of inflammation and coagulation in chronic HIV infection. The Journal of infectious diseases. 2014; 210(9):1396-406.
13. Nunes-Alves C, Nobrega C, Behar S M, Correia-Neves M. Tolerance has its limits: how the thymus copes with infection. Trends in immunology. 2013; 34(10):502-10.
14. Haas D W, Geraghty D E, Andersen J, Mar J, Motsinger A A, D'Aquila R T, et al. Immunogenetics of CD4 lymphocyte count recovery during antiretroviral therapy: An AIDS Clinical Trials Group study. The Journal of infectious diseases. 2006; 194(8):1098-107.
15. Rajasuriar R, Booth D, Solomon A, Chua K, Spelman T, Gouillou M, et al. Biological determinants of immune reconstitution in HIV-infected patients receiving antiretroviral therapy: the role of interleukin 7 and interleukin 7 receptor alpha and microbial translocation. The Journal of infectious diseases. 2010; 202(8):1254-64.
16. Isgro A, Aiuti A, Leti W, Gramiccioni C, Esposito A, Mezzaroma I, et al. Immunodysregulation of HIV disease at bone marrow level. Autoimmunity reviews. 2005; 4(8):486-90.
17. Isgro A, Leti W, De Santis W, Marziali M, Esposito A, Fimiani C, et al. Altered clonogenic capability and stromal cell function characterize bone marrow of HIV-infected subjects with low CD4+ T cell counts despite viral suppression during HAART. Clinical infectious diseases: an official publication of the Infectious Diseases Society of America. 2008; 46(12):1902-10.

18. Stanley S K, Kessler S W, Justement J S, Schnittman S M, Greenhouse J J, Brown C C, et al. CD34+ bone marrow cells are infected with HIV in a subset of seropositive individuals. Journal of immunology (Baltimore, Md.: 1950). 1992; 149:689-97.
19. Davis B R, Schwartz D H, Marx J C, Johnson C E, Berry J M, Lyding J, et al. Absent or rare human immunodeficiency virus infection of bone marrow stem/progenitor cells in vivo. Journal of virology. 1991; 65(4):1985-90.
20. De Luca A, Teofili L, Antinori A, Iovino M S, Mencarini P, Visconti E, et al. Haemopoietic CD34+ progenitor cells are not infected by HIV-1 in vivo but show impaired clonogenesis. British journal of haematology. 1993; 85(1):20-4.
21. Neal T F, Holland H K, Baum C M, Villinger F, Ansari A A, Saral R, et al. CD34+ progenitor cells from asymptomatic patients are not a major reservoir for human immunodeficiency virus-1. Blood. 1995; 86(5):1749-56.
22. von Laer D, Hufert F T, Fenner T E, Schwander S, Dietrich M, Schmitz H, et al. CD34+ hematopoietic progenitor cells are not a major reservoir of the human immunodeficiency virus. Blood. 1990; 76(7):1281-6.
23. Carter C C, Onafuwa-Nuga A, McNamara L A, Riddell Jt, Bixby D, Savona M R, et al. HIV-1 infects multipotent progenitor cells causing cell death and establishing latent cellular reservoirs. Nature medicine. 2010; 16(4):446-51.
24. Molina J M, Scadden D T, Sakaguchi M, Fuller B, Woon A, Groopman J E. Lack of evidence for infection of or effect on growth of hematopoietic progenitor cells after in vivo or in vitro exposure to human immunodeficiency virus. Blood. 1990; 76(12):2476-82.
25. Isgro A, Aiuti A, Mezzaroma I, Addesso M, Riva E, Giovannetti A, et al. Improvement of interleukin 2 production, clonogenic capability and restoration of stromal cell function in human immunodeficiency virus-type-1 patients after highly active antiretroviral therapy. British journal of haematology. 2002; 118(3):864-74.
26. Thiebot H, Louache F, Vaslin B, de Revel T, Neildez O, Larghero J, et al. Early and persistent bone marrow hematopoiesis defect in simian/human immunodeficiency virus-infected macaques despite efficient reduction of viremia by highly active antiretroviral therapy during primary infection. Journal of virology. 2001; 75 (23): 11594-602.
27. Adams G B, Pym A S, Poznansky M C, McClure M O, Weber J N. The in vivo effects of combination antiretroviral drug therapy on peripheral blood CD34+ cell colony-forming units from HIV type 1-infected patients. AIDS research and human retroviruses. 1999; 15(6):551-9.
28. Baillou C, Simon A, Leclercq V, Azar N, Rosenzwajg M, Herson S, et al. Highly active antiretroviral therapy corrects hematopoiesis in HIV-1 infected patients: interest for peripheral blood stem cell-based gene therapy. Aids. 2003; 17(4):563-74.
29. Bordoni V, Bibas M, Viola D, Sacchi A, Agrati C, Castelli G, et al. Chronic HIV-infected patients show an impaired dendritic cells differentiation of bone marrow CD34(+) cells. Journal of acquired immune deficiency syndromes (1999). 2013; 64(4):342-4.
30. Clark D R, Ampel N M, Hallett C A, Yedavalli V R, Ahmad N, DeLuca D. Peripheral blood from human immunodeficiency virus type 1-infected patients displays diminished T cell generation capacity. The Journal of infectious diseases. 1997; 176(3):649-54.
31. Clark D R, Repping S, Pakker N G, Prins J M, Notermans D W, Wit F W, et al. T-cell progenitor function during progressive human immunodeficiency virus-1 infection and after antiretroviral therapy. Blood. 2000; 96(1):242-9.
32. Costantini A, Giuliodoro S, Mancini S, Butini L, Regnery C M, Silvestri G, et al. Impaired in-vitro growth of megakaryocytic colonies derived from CD34 cells of HIV-1-infected patients with active viral replication. AIDS. 2006; 20(13):1713-20.
33. Isgro A, Mezzaroma I, Aiuti A, De Vita L, Franchi F, Pandolfi F, et al. Recovery of hematopoietic activity in bone marrow from human immunodeficiency virus type 1-infected patients during highly active antiretroviral therapy. AIDS research and human retroviruses. 2000; 16(15):1471-9.
34. Sauce D, Larsen M, Fastenackels S, Pauchard M, Ait-Mohand H, Schneider L, et al. HIV disease progression despite suppression of viral replication is associated with exhaustion of lymphopoiesis. Blood. 2011; 117(19): 5142-51.
35. Zauli G, Re M C, Davis B, Sen L, Visani G, Gugliotta L, et al. Impaired in vitro growth of purified (CD34+) hematopoietic progenitors in human immunodeficiency virus-1 seropositive thrombocytopenic individuals. Blood. 1992; 79(10):2680-7.
36. Yamakami K, Honda M, Takei M, Ami Y, Kitamura N, Nishinarita S, et al. Early bone marrow hematopoietic defect in simian/human immunodeficiency virus C2/1-infected macaques and relevance to advance of disease. Journal of virology. 2004; 78(20): 10906-10.
37. Thiebot H, Vaslin B, Derdouch S, Bertho J M, Mouthon F, Prost S, et al. Impact of bone marrow hematopoiesis failure on T-cell generation during pathogenic simian immunodeficiency virus infection in macaques. Blood. 2005; 105(6):2403-9.
38. Neben K, Heidbreder M, Muller J, Marxer A, Petry H, Didier A, et al. Impaired thymopoietic potential of immature CD3(-)CD4(+)CD8(-) T cell precursors from SIV-infected rhesus monkeys. International immunology. 1999; 11(9): 1509-18.
39. Knutsen A P, Roodman S T, Freeman J J, Mueller K R, Bouhasin J D Inhibition of thymopoiesis of CD34+ cell maturation by HIV-1 in an in vitro CD34+ cell and thymic epithelial organ culture model. Stem Cells. 1999; 17(6): 327-38.
40. Le T, Wright E J, Smith D M, He W, Catano G, Okulicz J F, et al. Enhanced CD4+ T-cell recovery with earlier HIV-1 antiretroviral therapy. The New England journal of medicine. 2013; 368:218-30.
41. Delaugerre C, Charreau I, Braun J, Nere M L, de Castro N, Yeni P, et al. Time course of total HIV-1 DNA and 2-long-terminal repeat circles in patients with controlled plasma viremia switching to a raltegravir-containing regimen. AIDS. 2010; 24(15):2391-5.
42. Delaugerre C, Gallien S, Flandre P, Mathez D, Amarsy R, Ferret S, et al. Impact of low-level-viremia on HIV-1 drug-resistance evolution among antiretroviral treated-patients. PloS one. 2012; 7(5):e36673.
43. Maillard I, Fang T, Pear W S. Regulation of lymphoid development, differentiation, and function by the Notch pathway. Annual review of immunology. 2005; 23:945-74.
44. Zamisch M, Moore-Scott B, Su D M, Lucas P J, Manley N, Richie E R. Ontogeny and regulation of IL-7-expressing thymic epithelial cells. J Immunol. 2005; 174(1):60-7.

45. Magri M, Yatim A, Benne C, Balbo M, Henry A, Serraf A, et al. Notch ligands potentiate IL-7-driven proliferation and survival of human thymocyte precursors. Eur J Immunol. 2009.
46. Lefort N, Benne C, Lelievre J D, Dorival C, Balbo M, Sakano S, et al. Short exposure to Notch ligand Delta-4 is sufficient to induce T-cell differentiation program and to increase the T cell potential of primary human CD34+ cells. Exp Hematol. 2006; 34(12):1720-9.
47. Benne C, Lelievre J D, Balbo M, Henry A, Sakano S, Levy Y. Notch increases T/NK potential of human hematopoietic progenitors and inhibits B cell differentiation at a pro-B stage. Stem cells (Dayton, Ohio). 2009; 27:1676-85.
48. Hunt P W, Brenchley J, Sinclair E, McCune J M, Roland M, Page-Shafer K, et al. Relationship between T cell activation and CD4+ T cell count in HIV-seropositive individuals with undetectable plasma HIV RNA levels in the absence of therapy. The Journal of infectious diseases. 2008; 197(1):126-33.
49. Thompson B A, Storm M P, Hewinson J, Hogg S, Welham M J, MacKenzie AB. A novel role for P2X7 receptor signalling in the survival of mouse embryonic stem cells. Cell Signal. 2012; 24(3):770-8.
50. Casati A, Frascoli M, Traggiai E, Proietti M, Schenk U, Grassi F. Cell-autonomous regulation of hematopoietic stem cell cycling activity by ATP. Cell death and differentiation. 2011; 18(3):396-404.
51. Lemoli R M, Ferrari D, Fogli M, Rossi L, Pizzirani C, Forchap S, et al. Extracellular nucleotides are potent stimulators of human hematopoietic stem cells in vitro and in vivo. Blood. 2004; 104(6):1662-70.
52. Rossi L, Salvestrini V, Ferrari D, Di Virgilio F, Lemoli R M. The sixth sense: hematopoietic stem cells detect danger through purinergic signaling. Blood. 2012; 120 (12):2365-75.
53. Yoon M J, Lee H J, Lee Y S, Kim J H, Park J K, Chang W K, et al. Extracellular ATP is involved in the induction of apoptosis in murine hematopoietic cells. Biol Pharm Bull. 2007; 30(4):671-6.
54. Mariathasan S, Weiss D S, Newton K, McBride J, O'Rourke K, Roose-Girma M, et al. Cryopyrin activates the inflammasome in response to toxins and ATP. Nature. 2006; 440(7081):228-32.
55. Martinon F, Burns K, Tschopp J. The inflammasome: a molecular platform triggering activation of inflammatory caspases and processing of proIL-beta. Mol Cell. 2002; 10(2):417-26.
56. Kaczmarek E, Koziak K, Sevigny J, Siegel J B, Anrather J, Beaudoin A R, et al. Identification and characterization of CD39/vascular ATP diphosphohydrolase. The Journal of biological chemistry. 1996; 271(51):33116-22.
57. Kukulski F, Levesque S A, Sevigny J. Impact of ectoenzymes on p2 and p1 receptor signaling. Advances in pharmacology (San Diego, Calif.). 2011; 61:263-99.
58. Borsellino G, Kleinewietfeld M, Di Mitri D, Sternjak A, Diamantini A, Giometto R, et al. Expression of ectonucleotidase CD39 by Foxp3+ Treg cells: hydrolysis of extracellular ATP and immune suppression. Blood. 2007; 110 (4):1225-32.
59. Deaglio S, Dwyer K M, Gao W, Friedman D, Usheva A, Erat A, et al. Adenosine generation catalyzed by CD39 and CD73 expressed on regulatory T cells mediates immune suppression. J Exp Med. 2007; 204(6):1257-65.
60. Dwyer K M, Deaglio S, Gao W, Friedman D, Strom T B, Robson S C. CD39 and control of cellular immune responses. Purinergic Signal. 2007; 3(1-2):171-80.
61. Mandapathil M, Szczepanski M J, Szajnik M, Ren J, Lenzner D E, Jackson E K, et al. Increased ectonucleotidase expression and activity in regulatory T cells of patients with head and neck cancer. Clinical cancer research: an official journal of the American Association for Cancer Research. 2009; 15(20):6348-57.
62. Le Moing V, Thiebaut R, Chene G, Sobel A, Massip P, Collin F, et al. Long-term evolution of CD4 count in patients with a plasma HIV RNA persistently <500 copies/mL during treatment with antiretroviral drugs. HIV medicine. 2007; 8(3):156-63.
63. Kaufmann G R, Perrin L, Pantaleo G, Opravil M, Furrer H, Telenti A, et al. CD4 T-lymphocyte recovery in individuals with advanced HIV-1 infection receiving potent antiretroviral therapy for 4 years: the Swiss HIV Cohort Study. Archives of internal medicine. 2003; 163(18): 2187-95.
64. Mendez-Lagares G, Garcia-Perganeda A, del Mar del Pozo-Balado M, Genebat M, Ruiz-Mateos E, Garcia Garcia M, et al. Differential alterations of the CD4 and CD8 T cell subsets in HIV-infected patients on highly active antiretroviral therapy with low CD4 T cell restoration. The Journal of antimicrobial chemotherapy. 2012; 67(5):1228-37.
65. Teixeira L, Valdez H, McCune J M, Koup R A, Badley A D, Hellerstein M K, et al. Poor CD4 T cell restoration after suppression of HIV-1 replication may reflect lower thymic function. Aids. 2001; 15(14):1749-56.
66. Gras L, Kesselring A M, Griffin J T, van Sighem A I, Fraser C, Ghani A C, et al. CD4 cell counts of 800 cells/mm3 or greater after 7 years of highly active antiretroviral therapy are feasible in most patients starting with 350 cells/mm3 or greater. Journal of acquired immune deficiency syndromes (1999). 2007; 45(2):183-92.
67. Mocroft A, Phillips A N, Gatell J, Ledergerber B, Fisher M, Clumeck N, et al. Normalisation of CD4 counts in patients with HIV-1 infection and maximum virological suppression who are taking combination antiretroviral therapy: an observational cohort study. The Lancet. 2007; 370(9585):407-13.
68. Kelley C F, Kitchen C M, Hunt P W, Rodriguez B, Hecht F M, Kitahata M, et al. Incomplete peripheral CD4+ cell count restoration in HIV-infected patients receiving long-term antiretroviral treatment. Clinical infectious diseases: an official publication of the Infectious Diseases Society of America. 2009; 48(6):787-94.
69. Ngowi B J, Mfinanga S G, Bruun J N, Morkve O. Immunohaematological reference values in human immunodeficiency virus-negative adolescent and adults in rural northern Tanzania. BMC infectious diseases. 2009; 9:1.
70. Benveniste O, Flahault A, Rollot F, Elbim C, Estaquier J, Pedron B, et al. Mechanisms involved in the low-level regeneration of CD4+ cells in HIV-1-infected patients receiving highly active antiretroviral therapy who have prolonged undetectable plasma viral loads. The Journal of infectious diseases. 2005; 191(10):1670-9.
71. Douek D C, McFarland R D, Keiser P H, Gage E A, Massey J M, Haynes B F, et al. Changes in thymic function with age and during the treatment of HIV infection. Nature. 1998; 396(6712):690-5.
72. Lelievre J D, Melica G, Itti E, Lacabaratz C, Rozlan S, Wiedemann A, et al. Initiation of c-ART in HIV-1 infected patients is associated with a decrease of the metabolic activity of the thymus evaluated using FDG-PET/computed tomography. Journal of acquired immune deficiency syndromes (1999). 2012; 61(1):56-63.

73. Li T, Wu N, Dai Y, Qiu Z, Han Y, Xie J, et al. Reduced thymic output is a major mechanism of immune reconstitution failure in HIV-infected patients after long-term antiretroviral therapy. Clinical infectious diseases: an official publication of the Infectious Diseases Society of America. 2011; 53(9):944-51.
74. Zhou H, Zhao H, Hao Y, Song C, Han J, Zhang J, et al. Excessive conversion and impaired thymic output contribute to disturbed regulatory T-cell homeostasis in AIDS patients with low CD4 cell counts. AIDS. 2013; 27(7): 1059-69.
75. Zauli G, Vitale M, Gibellini D, Capitani S. Inhibition of purified CD34+ hematopoietic progenitor cells by human immunodeficiency virus 1 or gp120 mediated by endogenous transforming growth factor beta 1. J Exp Med. 1996; 183(1):99-108.
76. Dorival C, Brizzi F, Lelievre J D, Sol-Foulon N, Six E, Henry A, et al. HIV-1 Nef protein expression in human CD34+ progenitors impairs the differentiation of an early T/NK cell precursor. Virology. 2008; 377(1):207-15.
77. Rajasuriar R, Booth D R, Gouillou M, Spelman T, James I, Solomon a, et al. The role of SNPs in the α-chain of the IL-7R gene in CD4+ T-cell recovery in HIV-infected African patients receiving suppressive cART. Genes and immunity. 2012; 13:83-93.
78. Limou S, Melica G, Coulonges C, Lelievre J D, Do H, McGinn S, et al. Identification of IL7RA risk alleles for rapid progression during HIV-1 infection: a comprehensive study in the GRIV cohort. Current HIV research. 2012; 10(2):143-50.
79. Yatim A, Benne C, Sobhian B, Laurent-Chabalier S, Deas O, Judde J G, et al. NOTCH1 nuclear interactome reveals key regulators of its transcriptional activity and oncogenic function. Mol Cell. 2012; 48(3):445-58.
80. Mendez-Lagares G, Romero-Sanchez M C, Ruiz-Mateos E, Genebat M, Ferrando-Martinez S, Munoz-Fernandez M A, et al. Long-term suppressive combined antiretroviral treatment does not normalize the serum level of soluble CD14. The Journal of infectious diseases. 2013; 207(8): 1221-5.
81. Di Virgilio F. Liaisons dangereuses: P2X(7) and the inflammasome. Trends Pharmacol Sci. 2007; 28(9):465-72.
82. Delarasse C, Gonnord P, Galante M, Auger R, Daniel H, Motta I, et al. Neural progenitor cell death is induced by extracellular ATP via ligation of P2X7 receptor. Journal of neurochemistry. 2009; 109(3):846-57.
83. Coppi E, Pugliese A M, Urbani S, Melani A, Cerbai E, Mazzanti B, et al. ATP modulates cell proliferation and elicits two different electrophysiological responses in human mesenchymal stem cells. Stem Cells. 2007; 25(7): 1840-9.
84. Pedata F, Melani A, Pugliese A M, Coppi E, Cipriani S, Traini C. The role of ATP and adenosine in the brain under normoxic and ischemic conditions. Purinergic Signal. 2007; 3(4):299-310.
85. Namen A E, Lupton S, Hjerrild K, Wignall J, Mochizuki D Y, Schmierer A, et al. Stimulation of B-cell progenitors by cloned murine interleukin-7 Nature. 1988; 333(6173): 571-3.
86. Puel A, Ziegler S F, Buckley R H, Leonard W J. Defective IL7R expression in T(−)B(+)NK(+) severe combined immunodeficiency. Nature genetics. 1998; 20(4):394-7.
87. Roffman C M, Zhang J, Chitayat D, Sharfe N. A partial deficiency of interleukin-7R alpha is sufficient to abrogate T-cell development and cause severe combined immunodeficiency. Blood. 2000; 96(8):2803-7.
88. Younas M, Hue S, Lacabaratz C, Guguin A, Wiedemann A, Surenaud M, et al. IL-7 modulates in vitro and in vivo human memory T regulatory cell functions through the CD39/ATP axis. J Immunol. 2013; 191(6):3161-8.
89. Keil R, Schulz J, Hatzfeld M. p0071/PKP4, a multifunctional protein coordinating cell adhesion with cytoskeletal organization. Biological chemistry. 2013; 394(8):1005-17.
90. Hanai N, Nagata K, Kawajiri A, Shiromizu T, Saitoh N, Hasegawa Y, et al. Biochemical and cell biological characterization of a mammalian septin, Septl 1. FEBS letters. 2004; 568(1-3):83-8.
91. Liu Y, Wang B, Wang J, Wan W, Sun R, Zhao Y, et al. Down-regulation of PKCzeta expression inhibits chemotaxis signal transduction in human lung cancer cells. Lung cancer (Amsterdam, Netherlands). 2009; 63(2):210-8.
92. Feau S, Schoenberger S P, Altman A, Becart S. SLAT regulates CD8+ T cell clonal expansion in a Cdc42- and NFAT1-dependent manner. J Immunol. 2013; 190(1):174-83.
93. Sultan F A, Sweatt J D. The role of the Gadd45 family in the nervous system: a focus on neurodevelopment, neuronal injury, and cognitive neuroepigenetics. Advances in experimental medicine and biology. 2013; 793:81-119.
94. Bisbal C, Silverman R H. Diverse functions of RNase L and implications in pathology. Biochimie. 2007; 89(6-7): 789-98.
95. Labbe K, McIntire C R, Doiron K, Leblanc P M, Saleh M. Cellular inhibitors of apoptosis proteins cIAP1 and cIAP2 are required for efficient caspase-1 activation by the inflammasome. Immunity. 2011; 35 (6): 897-907.
96. North R A, Jarvis M F. P2X receptors as drug targets. Molecular pharmacology. 2013; 83(4):759-69.
97. Keystone E C, Wang M M, Layton M, Hollis S, McInnes I B. Clinical evaluation of the efficacy of the P2X7 purinergic receptor antagonist AZD9056 on the signs and symptoms of rheumatoid arthritis in patients with active disease despite treatment with methotrexate or sulphasalazine. Ann Rheum Dis. 2012; 71(10):1630-5.
98. Karanu F N, Murdoch B, Miyabayashi T, Ohno M, Koremoto M, Gallacher L, et al. Human homologues of Delta-1 and Delta-4 function as mitogenic regulators of primitive human hematopoietic cells. Blood. 2001; 97(7): 1960-7.
99. Kok A, Hocqueloux L, Hocini H, Carriere M, Lefrou L, Guguin A, et al. Early initiation of combined antiretroviral therapy preserves immune function in the gut of HIV-infected patients. Mucosal immunology. 2015; 8(1):127-40.

The invention claimed is:

1. A method of restoring T-cell lymphopoiesis in a subject infected with human immunodeficiency virus (HIV), wherein a combined antiretroviral treatment (c-ART) suppresses viral replication in said subject but peripheral CD4+ T-cell counts fail to return to a level above AIDS-defining, comprising
administering to the subject a therapeutically effective amount of a P2X7 receptor antagonist,
inducing CD4+ T-cell lymphopoiesis.

2. A method for the prophylactic treatment of acquired immune deficiency syndrome in a subject infected with human immunodeficiency virus (HIV), wherein viral replication in said subject is suppressed with combined antiretroviral treatment (c-ART) but the subject has poor immunological CD4+ T-cell restoration, wherein CD4+ T-cell levels are below 500 cells/mm³, comprising
    administering to the subject a therapeutically effective amount of a P2X7 receptor antagonist,
    inducing CD4+ T-cell lymphopoiesis, and
    maintaining peripheral CD4+ T-cells counts of at least 500 cells/mm³.

3. The method of claim 1, further comprising confirming induction of CD4+ T-cell lymphopoiesis when a peripheral CD4+ T-cell count is at least 200 cells/mm³.

4. The method of claim 1, further comprising confirming induction of CD4+ T-cell lymphopoiesis when a peripheral CD4+ T-cell count is at least 500 cells/mm³.

\* \* \* \* \*